United States Patent [19]

Bennett et al.

[11] Patent Number: 5,530,114

[45] Date of Patent: Jun. 25, 1996

[54] OLIGONUCLEOTIDE MODULATION OF ARACHIDONIC ACID METABOLISM

[75] Inventors: Clarence F. Bennett; David J. Ecker; Stanley T. Crooke, all of Carlsbad; Christopher K. Mirabelli, Encinitas, all of Calif.

[73] Assignee: Isis Pharmaceuticals, Inc., Carlsbad, Calif.

[21] Appl. No.: 847,055

[22] PCT Filed: Apr. 17, 1991

[86] PCT No.: PCT/US91/02628

§ 371 Date: Apr. 3, 1992

§ 102(e) Date: Apr. 3, 1992

[87] PCT Pub. No.: WO91/16901

PCT Pub. Date: Nov. 14, 1991

Related U.S. Application Data

[63] Continuation of Ser. No. 516,969, Apr. 30, 1990, abandoned.

[51] Int. Cl.$^6$ .......................... C07H 21/04; A61K 48/00; C12Q 1/68
[52] U.S. Cl. ............................ 536/24.3; 536/24.1; 435/6
[58] Field of Search ............................ 536/24.31, 24.1; 514/44; 435/6

[56] References Cited

PUBLICATIONS

Uhlmann et al. (Jun. 1990) Chemical Reviews 90:544–584.
Hoshiko et al. (Dec. 1990) P.N.A.S. 87:9073–9077.
Rather, M. (Mar. 1989) Bio/Technology, 7:207.
Stein et al. (20 Aug. 1993) Science 261:1004–1021.
Chubb et al. (Apr. 1992) TibTech 10:132–136.
Aiyar et al., Solubilization of rat liver vasopressin receptors as a complex with a guanine–nucleotide–binding protien and phosphoinoside–specific phospholipase C, *Biochem. J.,* 261:63–70, 1989.
Archer et al., Accumulation of inflammatory cells in respone to intracutaneous platelet activating factor (Paf–acether) in man, *Br. J. Dermatol.,* 112:285–290, 1985.
Balcarek et al., Isolation and characterization of a cDNA clone encoding rat 5-lipoxygenase, *J. Biol. Chem.,* 263:13937–13941, 1988.
Barst and Mullane, The Release of a leukotriene $D_4$–like substance following myocardial infarction in rabbits, *Eur. J. Pharmacol.,* 114:383–387, 1985.
Bell et al., Diglyceride lipase: A pathway for arachidontae release from human platelets, *Proc. Natl. Acad. Sci. U.S.A.,* 76:3238–3241.
Bennett et al., Differential effects of manoalide on secreted and intracellular phospholipases, *Biochem. Pharm.,* 36:733–740, 1987.
Bennett and Crooke, Purification and characterization of a phosphoinositide–specific phospholipase C from guinea pig uterus, *J. Biol. Chem.,* 262:18789–13797, 1987.
Berridge et al., Changes in levels of inositol phosphates after agonist–dependent hydrolysis of membrane phosphoinositides, *Biochem. J.,* 212:473–482, 1983.

Berridge, Inositol Trisphosphate and Diacylglycerol: Two interacting second messangers, *Ann. Rev. Biochem.,* 56:159–193, 1987.
Black, Leukotriene $C_4$ Induces Vasogenic Cerebral Edema in Rats, *Prostaglandins Leukotriene Med.,* 14:339–340, 1984.
Bonaa et al., Effect of Eicosapentaenoic and Docosahexaenoic Acids on Blood Pressure in Hypertension, *New Eng. J. Med.,* 322:795–801, 1990.
Braquet et al., The Promise of Platelet–Activating Factor, *ISI Atlas of Science: Pharmacology,* 187–198, 1987.
Burke et al., Leukotrienes $C_4$, $D_4$ and $E_4$: Effects on Human and Guinea–Pig Crdiac Preparation in vitro, *J. Pharmacol. Exper. Therap.,* 221:235–241, 1982.
Camp et al., Responses of human skin to intradermal injection of leukotrienes $C_4$, $D_4$ and $B_4$; *Br. J. Pharmacol.,* 80:497–502, 1983.
Chilton and Connell, 1–Ether–linked Phosphoglycerides, *J. Biol. Chem.,* 263:5260–5265, 1988.
Crooke and Bennett, Mammalian phosphoinositide–specific phospholipase C isoenzymes, *Cell Calcium,* 10:309–323, 1989.
Crunkhorn and Willis, Cutaneous reactions to intradermal prostaglandins, *Br. J. Pharmacol.,* 41:49–56, 1971.
Cuss et al., Effects of inhaled platelet activating factor on pulmonary function and bronchial responsiveness in man, *Lancet,* 2:189, 1986.
Dahlen et al., Allergen challenge of lung tissue from asthmatics elicits bronchial contraction that correlates with the release of leukotrienes $C_4$, $D_4$ and $E_4$, *Proc. Natl. Acad. Sci. U.S.A.,* 80:1712–1716, 1983.
Dahlen et al., Leukotrienese are potent constrictors of human bronchi, *Nature,* 288:484–486, 1980.

(List continued on next page.)

*Primary Examiner*—W. Gary Jones
*Assistant Examiner*—Lisa Arthur
*Attorney, Agent, or Firm*—Law Offices of Jane Massey Licata

[57] ABSTRACT

Compositions and methods are provided for the treatment and diagnosis of diseases amenable to modulation of the synthesis or metabolism of arachidonic acid and related compounds. In accordance with preferred embodiments, oligonucleotides and oligonucleotide analogs are provided which are specifically hybridizable with nucleic acids encoding 5-lipoxygenase, 5-lipoxygenase activating proteins, $LTA_4$ hydrolase, phospholipase $A_2$, phospholipase C, and coenzyme A-independent transacylase. The oligonucleotide comprises nucleotide units sufficient in identity and number to effect said specific hybridization. In other preferred embodiments, the oligonucleotides are specifically hybridizable with a transcription initiation site, a translation initiation site, and intron/exon junction. Methods of treating animals suffering from disease amenable to therapeutic intervention by modulating arachidonic acid synthesis or metabolism with an oligonucleotide or oligonucleotide analog specifically hybridizable with RNA or DNA corresponding to one of the foregoing proteins are disclosed. Methods for treatment of diseases responding to modulation of arachidonic acid synthesis or metabolism are disclosed.

1 Claim, 25 Drawing Sheets

OTHER PUBLICATIONS

Davidson et al., Lerukotriene B$_4$, a mediator of inflammation present in synovial fluid in rheumatoid arthritis, *Ann. Rheum. Dis.*, 42:677–679, 1983.

Dixon et al., Cloning of the cDNA for human 5–lipoxygenase, *Proc. Natl. Acad. Sci. USA*, 85:416–420, 1988.

Dixon et al., Requirement of a 5–lipoxygenase–activating protein for leukotriene synthesis, *Nature*, 343:282–284, 1990.

Emori et al., A second type of rat phospholinositide–specific phospholipase C containing a src–related sequence not essential for phosphoinositide–hydrolyzing activity, *J. Biol. Chem.*, 264:21885–21890.

Ford–Hutchinson, A. W., Leukotriene B$_4$ in inflammation, *Crit. Rev. in Immunol.*, 10:1–12, 1989.

Franson et al., Isolation and characterization of a phospholipase A$_2$ from an inflammatory exudate, *J. Lipid Res.*, 19:18–23, 1978.

Funk et al., Characterization of the human 5–lipoxygenase gene, *Proc. Natl. Acad. Sci. USA*, 86:2587–2591, 1989.

Funk et al., Molecular cloning and amino acid sequence of leukotriene A$_4$ hydrolase, *Proc. Natl. Acad. Sci USA*, 84:6677–6881, 1987.

Hoffman and Majerus, Identification adn properties of two district phosphatidylinositol–specific phospholipase C enzymes from sheep seminal vesicular glands, *J. Biol. Chem.*, 257:6461–6469, 1982.

Hogaboom et al., Purification, Characterization, and Structural Properties of a Singel Protein from Rat Basophilic Leukemia (RBL–1) Cells Possessing 5–Lipoxygenase and Leukotriene A$_4$ Synthetase Activities, *Mol. Pharmacol.*, 30:510–519, 1986.

Humes et al., Evidence for Two Sources of Areachidonic Acid for Oxidative Metabolism by Mouse Peritoneal Macrophages, *J. Biol. Chem.*, 257:1591–1594.

Klickstein et al., Lipoxygenation of arachidonic acid as a source of polymorphonuclear leukocyte chemotactic factors in synovial fluid and tissue in reheumatoid arthritis and spondyloarthritis, *J. Clin. Invest.*, 66:1166–1170, 1980.

Kragballe and Herlin, Benoxaprofen Improves Psoriasis, *Arch. Dermatol.*, 119:548–552, 1983.

Kramer et al., Structure and Properties of a Human Non–pancreatic phospholipase A$_2$, *J. Biol. Chem.*, 264:5768–5775, 1989.

Letts and Piper, The actions of leukotrienes C$_4$ and D$_4$ on guinea–pig isolated hearts, *Br. J. Pharmacol.*, 76:169–176, 1982.

Mahadevappa and Holub, Diacylglycerol Lipase Pathway in a Minor Source of Release Arachidonic Acid in Thrombin–Stimulated Human Platelets, *Biochem. Biophys. Res. Comm.*, 134:1327–1333, 1986.

Mallet et al., Platelet Activating Factor in Chronic Plaque Psoriasis, *Adv. in Prostaglandins, Thromboxanes, Leukotrienes and Related Compounds*, vol. 17B:640–642, 1987.

Margolis et al., EGF Induces Tyrosine Phosphorylation of Phospholipase C–11: A potential mechanism for EGF receptor signaling, *Cell*, 57:1101–1107, 1989.

Marone et al., Cardiovascular and Metabolic Effects of Peptide Leukotrienes in *Man, Biology of the Leukotrienes*, ed. by R. Levi and R. D. Krell, Ann. New York Acad. Sci. 524, pp. 321–323, New York Academy of Sciences, New York, 1988.

Matsumoto et al., Molecular cloning and amino acid seqeucne of human 5–lioxygenase, *Proc. Natl. Acad. Sci. USA*, 85:26–30, 1988.

McGee and Fitzpatrick, Enzymatic Hydration of Leukotriene A$_4$, *J. Biol. Chem.*, 260:12832–12837.

Miller et al., Identification and isolation of a membrane protein necessary for leukotriene production, *Nature*, 343:276–281, 1990.

Minami et al., Molecular cloning of a cDNA coding for huamn leukotriene A$_4$ hydrolase, *J. Biol. Chem.*, 262:13873–13876, 1987.

Mong et al., Characterization of the leukotriene D$_4$ receptor in guinea–pig lung, *Eur. J. Pharmacol.*, 102:1–11, 1984.

Ohishi et al., Leukotriene A$_4$ hydrolase in the human lung, *J. Biol. Chem.*, 262:10200–10205, 1987.

Ohta et al., Complete cDNA encoding a putative phospholipase C from transformed human lymphocytes, *FEBS Lett.*, 242:31–35, 1988.

Palmer et al., Electrophysiological response of cerebellar purkinje neurons to leukotriene D$_4$ adn B$_4$, *J. Pharmacol. Exp. Ther.*, 219:91–96, 1981.

Pruzanski and Vadas, Secretory synovial fluid phospholipase A$_2$ and its role in the pathogenesis of inflammation in arthritis, *J. Rheumatol.*, 15:1601–1603, 1988.

Radmark et al., Leukotriene A$_4$ hydrolase in human leukocytes, *J. Biol. Chem.*, 259:12339–12345, 1984.

Rangi et al., Suppression by ingested eicosapentaenoic acid of the increases in nasal mucosal blood flow and eosinophilia of ryegrass–allergic reactions, *J. Allergy Clin. Immunol.*, 85:484–489, 1990.

Rhee et al., Studies of inositol phospholipid–specific phospholipase C, *Science*, 244:546–550, 1989.

Rosam et al., Potent ulcerogenic actions of platelet–activating factro on the stomach, *Nature*, 319:54–56, 1986.

Roth and Leffer, Studies on the mechanism of leukotriene induced coronary artery constriction, *Prostaglandins*, 26:573–581, 1983.

Rothenberg et al., Oligonucleotides as anti–sense inhibitors of gene expression: therapeutic implications, *J. Natl. Cancer Inst.*, 81:1539–1544, 1989.

Rouzer and Samuelsson, On the nature of the 5–lipoxygenase reaction in human leukocytes: enzyme purification and requirement for multiple stimulatory factors, *Proc. Natl. Acad. Sci. U.S.A.*, 82:6040–6044, 1985.

Rouzer et al., On the nature of the 5–lipoxygenase reaction in human leukocytes: characterization of a membrane–associate stimulatory factor, *Proc. Natl. Acad. Sci. USA*, 82:7505–7509, 1985.

Rouzer and Samuelsson, Reversible, calcium–dependent membrane association of human leukocyte 5–lipoxygenase, *Proc. Natl. Acad. Sci. USA*, 84:7393–7397, 1987.

Rouzer and Kargman, translocation of 5–lipoxygenase to the membrane in human leukocytes challenged with ionophore A23187, *J. Biol. Chem.*, 263:10980–10988, 1988.

Rouzer et al., MK886, A potent and specific leukotriene biosynthesis inhibitor blocks and reverses the membrane association of 5–lipoxygenase in ionophore–challenged leukocytes, *J. Biol. Chem.*, 265:1436–1442, 1990.

Sasaki et al., Detection of leukotriene B$_4$ in cardiac tissues and its role in infarct extension through leucocyte migration, *Cardiovasc. Res.*, 22:142–148, 1988.

Schellenberg and Foster, Differential activity of leukotrienes upon human pulmonary vein and artery, *Prostaglandins*, 27:475–482, 1984.

Seilhamer et al., Cloning and recombinant expression of phospholipase $A_2$ present in rheumatoid arthritic synovial fluid, *J. Biol. Chem.*, 264:5335–5338, 1989.

Sirois et al., Pharmacological activity of leukotrienes $A_4$, $B_4$, $C_4$ and $D_4$ on sleected guinea–pig, rat, rabbit, and human smooth muscles, *Prost. Leuk. Med.*, 7:327–340, 1981.

Skerrett et al., Arachidonic Acid Metabolism, Cytokine Release, and Antimicrobial Activity, *J. Immunol.*, 144:1052–1061, 1990.

Smith et al., Beneficial Effects of the Peptidoleukotriene Receptor Antagonist, Sk&F 104353, on the responses to experimental endotoxemia in the conscious rat. *Circ. Shock*, 25:21–31, 1988.Sugiura et al., Transacylation of lyso platelet–activating factor and other lysophosphilipids by macrophage microsomes, *J. Biol. Chem.*, 262:1199–1205, 1987.

Terano et al., Effect of orally administered eicosapentaenoic acid (EPA) on the formation of leukotriene $B_4$ and leukotriene $B_5$ by rat leukocytes, *Biochem. Pharmacol.*, 33:3071–3076, 1984.

Ueda et al., Purification of arachidonate 5–lioxygenase from porcine leukocytes and its reactivity with hydroperoxyeicosatetraenoic acids, *J. Biol. Chem.*, 261:7982–7988, 1986.

Wahl et al., Epidermal growth factor stimulates tyrosine phosphorylation of phospholipase C–II independently of receptor internalization and extracellular calcium, *Proc. Natl. Acad. Sci. USA*, 86:1568–1572, 1989.

Wallace et al., Evidence for platelet–activating factor as a mediator of endotoxin–induced gastrointestinal damage in the rat, *Gastroenterology*, 1987 in press.

Wong et al., Interaction of 5–lipoxygenase with membranes: studies on the association of soluble enzyme with membranes and alterations in enzyme activity, *Biochemistry*, 27:6763–6769, 1988.

Zon, G., Oligonucleotide analogues as potential chemotherapeutic agents, *Pharmaceutical Res.*, 5:539–549.

FIG. 3A

```
                                    TAGATGCGGA CACCTGGACC GCCGGCGCCGA GGCTCCCGGC GCTCGCTGCT CCCGGGGCCC GCGCC
ATG CCC TCC TAC ACG GTC ACC GTG GCC CAG TTC GCC GGC ACT GAC GAC TAC ATC TAC CTC
met pro ser tyr thr val thr val ala gln phe ala gly thr asp asp tyr ile tyr leu AGC CTC GTG GGC TCG GCG GGC TGC AGC AAG GAG CTG GAC AAG CCC TTC TAC AAC GAC TTC GAG CGT
ser leu val gly ser ala gly cys ser glu leu asp lys his leu leu asp lys pro phe tyr asn asp phe glu arg INTRON A (8kb)

GGC GCG GTG GAT TCA TAC GAC GTG ACT GTG GAC GAG GAA CTG GGC GAG ATC CAG CTG GTC AGA ATC GAG AAG
gly ala val asp ser tyr asp val thr val asp glu glu leu gly glu ile gln leu val arg ile glu lys CGA AAG TAC TGG CTG AAT GAC GAC TGG ATC TAC CTG AAG TAC ATC ACG AAG CTG ACG CCC CAC GGG GAC TAC ATC
arg lys tyr trp leu asn asp asp trp ile tyr leu lys tyr ile thr lys leu thr pro his gly asp tyr ile INTRON B (13kb)

GAG TTC CCC TGC TAC CGC TGG ATC ACC GGC GAT GTC GAG GTT GTC CTG AGG GAT GGA CGC GCA AAG TTG GCC
glu phe pro cys tyr arg trp ile thr gly asp val glu val val leu arg asp gly arg ala lys leu ala INTRON C (> 26kb)

CGA GAT GAC CAA ATT CAC ATT CTC AAG CAA CAC CGA AAA GAA CTG GAA ACA CGG CAA AAA CAA TAT CGA
arg asp asp gln ile his ile leu lys gln his arg lys glu leu glu thr arg gln lys gln tyr arg TGG ATG GAG TGG AAC CCT GGC TTC CCC GGG TTA ATC GAT GCC AAA TGC CAC AAG GAT TTA CCC CGT GAT ATC
trp met glu trp asn pro gly phe pro gly leu ser ile asp ala lys cys his lys asp leu pro arg asp ile INTRON D (12kb)

CAG TTT GAT AGT GAA AAA GGA GTG GAC TTT GTT CTG AAT TAC TCC AAA GCG ATG GAG AAC CTG TTC ATC AAC
gln phe asp ser glu lys gly val asp phe val leu asn tyr ser lys ala met glu asn leu phe ile asn CGC TTC ATG CAC ATG CAG TTC TCT TCT GAC TTC GCC GAC TTT GAG AAA ATC TTT GTC AAG ATC AGC
arg phe met his met gln phe ser ser asp phe ala asp phe glu lys ile phe val lys ile ser
```

FIG. 3B

```
               INTRON E (0.8kb)
                  /
AAC ACT ATT TCT GAG CGG GTC ATG AAT CAC TGG CAG GAA GAC CTG ATG TTT GGC TAC CAG TTC CTG AAT GGC
asn thr ile ser glu arg val met asn his trp gln glu asp leu met phe gly tyr gln phe leu asn gly TGC AAC CCT GTG TTG ATC CGG CGC TGC ACA GAG GTC TGC CCC GAG AAG CTG ACA GAG ACG GAG ATG GTA GAG
cys asn pro val leu ile arg arg cys thr glu val cys pro glu lys leu thr glu thr glu met val glu
                                                    INTRON F (4kb)
                                                       /
TGC AGC CTG GAG CGG CAG CTC AGC TTG GAG CAG GTC CAA CAA GGG AAC ATT TTC ATC GTG GAC TTT GAG
cys ser leu glu arg gln leu ser leu glu gln val gln gln gly asn ile phe ile val asp phe glu CTG CTG GAT GGC ATC GAT GCC AAC ACA GAC CCC ACA CTC CAG TTC CTG GCC GCT CCC ATC TGC TTG
leu leu asp gly ile asp ala asn thr asp pro thr leu gln phe leu ala ala pro ile cys leu
                                                              INTRON G (11kb)
                                                                 /
CTG TAT AAG AAC CTG GCC AAC AAG ATT GTC CCC ATT CAG CTC AAC CAA ATC CCG GGA GAT GAG AAC
leu tyr lys asn leu ala asn lys ile val pro ile gln leu asn gln ile pro gly asp glu asn CCT ATT TTC CTC CCT TCG GAT GCA AAA TAC TGG CTT TTG GCC AAA ATC TGG GTG CGT TCC AGT GAC TTC
pro ile phe leu pro ser asp ala lys tyr trp leu leu ala lys ile trp val arg ser ser asp phe CAC GTC CAC CAG ACC ATC ACC CAC CTT CGA ACA CAT CTG GTG TCT GAG GTT TTT GGC ATT GCA ATC TAC
his val his gln thr ile thr his leu arg thr his leu val ser glu val phe gly ile ala met tyr
                                     INTRON H (1.7kb)
                                        /
CGC CAG CTG CCT GCT GTG CAC CCC ATT TTC AAG CTG GTG GCA CAC GTG GCA AGA TTC ACC ATT GCA ATC AAC
arg gln leu pro ala val his pro ile phe lys leu val ala his val ala arg phe thr ile ala ile asn
   INTRON I (1.0kb)
    /
ACC AAG GCC CGT GAG CAG CTC ATC TGC GAG TGT GGC CTC TTT GAC TTC TTC GAC AAG GCC ACA GGG GGC GGT GGG
thr lys ala arg glu gln leu ile cys glu cys gly leu phe asp phe phe asp lys ala thr gly gly gly gly
```

FIG. 3C

```
CAC GTG CAG ATG GTG CAG AGG GCC ATG AAG GAC CTG ACC TAT GCC TCC CTG TGC TTT CCC GAG GCC ATC AAG
his val gln met val gln arg ala met lys asp leu thr tyr ala ser leu cys phe pro glu ala ile lys GCC CGG GGC ATG GAG AGC AGC GAA GAA AGC TTG GAA GAC ATC CCC TAC TTC TAC GAC GAC GGG CTC CTG GTG GAA
ala arg gly met glu ser ser glu glu ser leu glu asp ile pro tyr phe tyr arg asp asp gly leu leu val trp glu INTRON J (0.2kb)

GCC ATC AGG ACG TTC ACG GAG GTG GTA GAC ATC TAC TAC GAG GGC GAC CAG GTG GAG GAC CCG
ala ile arg thr phe thr glu val val asp ile tyr tyr glu gly asp gln val glu asp pro INTRON K (0.2kb)

GAG CTG CAG GAC TTC GTG AAC GAT GTC TAC GTG TAC GGC ATG CGG GGC CGC AAG TCC TCA GGC TTC CCC AAG
glu leu gln asp phe val asn asp val tyr val tyr gly met arg gly arg lys ser ser gly phe pro lys TCG GTC AAG AGC CGG GAG CAG CTG TCG GAG TAC CTG TAC CTG TTC ACC GCC TCC GCC CAG CAC GCC
ser val lys ser arg glu gln leu ser glu tyr leu tyr leu phe thr ala ser ala gln his ala GCG GTC AAC TTC GGC CAG TAC GAC TGG TGC TCC ATC CCC AAT GCG CCC ACC ATG CGA GCC CCG CCA
ala val asn phe gly gln tyr asp try cys ser trp ile pro asn ala pro thr met arg ala pro pro CCG ACT GCC AAG GGC GTG GTG ACC ATT GAG CAG ATC GAG CTG CCC GAC CGC GGC CGC TCC TGC TGG
pro thr ala lys gly val val thr ile glu gln ile glu val asp thr arg gly arg ser cys trp INTRON L (0.3kb)                                INTRON M (1.3 kb)

CAT CTG GGT GCA GTG TGG GCG CTG AGC CTG TGG GCG CTG TTC CTG ATG TAC CCA GAA GAG
his leu gly ala val trp ala leu ser leu trp ala leu phe leu met tyr pro glu glu CAT TTT ATC GAG AAG CCT GTG AAG GAA TTC CGA ATG GCC TTC CGC AAG CTC GAG GCC ATT GTC AGC GTG
his phe ile glu lys pro val lys glu phe arg met ala phe arg lys leu glu ala ile val ser val ATT GCT GAG CGC AAC AAG AAG AAG CAG CTG CCA TAT TAC TTG TCC CCA GAC CGG ATT CCG AAC AGT GTG
ile ala glu arg asn lys lys lys gln leu pro tyr tyr leu ser pro asp arg ile pro asn ser val
```

```
GCC ATC TGA GCACACTGCC AGTCTCACTG TGGGAAGGCC AGCTGCCCCA GCCAGATGGA CTCCAGCCTG CCTGGCAGGT
ala ile ***

GTCTGGCCAG GCCTCTTGGC AGTCACATCT CTTCCTCCGA GGCCAGTACC TTTCCATTTA TTCTTTGATC TTCAGGGAAC

TGCATAGATT GATCAAAGTG TAAACACCAT AGGGACCCAT TCTACACAGA GCAGGACTGC ACAGCGTCCT GTCCACACCC

AGCTCAGCAT TTCCACACCA AGCAGCAACA GCAAATCACG ACCACTGATA GATGTCTATT CTTGTTGGAG ACATGGGATG

ATTATTTTCT GTTCTATTTG TGCTTAGTCC AATTCCTTGC ACATAGTAGG TACCCAATTC AATTACTATT GAATGAATTA

AGAATTGGTT GCCATAAAAA TAAATCAGTT CATTTAAAAA
```

Fig. 3D

```
                                          intron 1 (0.2 kb)
     1                                    /                  41                                           61
     AACTCTGGAGTCCTCTGAGAGAGCCACCAAGGAGGAGCAGGCCGGGGCAGAAGTTGAGAC 81                                    101                                121
     CACCCAGCAGGAGCTAGGCCAGTCCATCTGCATTTGTCACCCAGAACTCTTACCATGAAGACCCTCC
                                                                      MetLysThrLeuL intron 2 (0.25 bp)
     141                          161    /                    181                                   201
     TACTGTTGGCAGTGATCATGATCTTTGCCTACTGCAGGCCCATGGAATTTGTGAATTTCCACAGAAT
     euLeuLeuAlaValIleMetIleThrGlyLeuLeuGlnAlaHisGlyAsnLeuValAlaAsnPheHisArgMe 221                                241                                   261
     GATCAAGTTGACGACAGGAAAGGAAGCCGCACTCAGTTATGGCTTCTACGGCTGCCACTGTGGCGTGGGT
     tIleLysLeuThrThrGlyLysLysGluAlaAlaLeuSerTyrGlyPheTyrGlyCysHisCysGlyValGly
                                                                intron 3 (2.2 kb)
     281                                301                /               321                          341
     GGCAGAGGATCCCCAAGGATGCAACGGATCGCTGCTGTGTCACTCATGACTGTTGCTACAAACGTCTGG
     GlyArgGlySerProLysAspAlaThrAspSerCysValThrHisAspCysCysTyrLysArgLeuG intron 4
     361                                381                                    401                /
     AGAAACGTGGATGTGGCACCAAATTTCTGAGCTACAAGTTTAGCAACTCGGGAGCAGAATCACCTGTGC
     luLysArgGlyCysGlyThrLysPheLeuSerTyrLysPheSerAsnSerGlySerArgIleThrCysAl 421                                441                                   461                              481
     AAAACAGGACTCCTGCAGAAGTCAACTGTGTGAGTGTGATAAGGCTGCCACCTGTTTTGCTAGAAAC
     aLysGlnAspSerCysArgSerGlnLeuCysGluCysAspLysAlaAlaAlaThrCysPheAlaArgAsn 501                               521                               541
     AAGACGACCTACAATAAAAGTACCAGTACTATTCCAATAAACACTGCAGAGGAGCACCCTGTTGCT
     LysThrThrTyrAsnLysLysTyrGlnTyrTyrSerAsnLysHisCysArgGlySerThrProArgCys*

561                               581                          601                                   621
     GAGTCCCCTCCTTCCCTGGAAACCTTCCACCCAGTGCTGAATTTCCCTTCTCTCATACCCTCCCTCCCTACC
```

FIG. 4A

```
641
CTAACCAAGTTCCTTGGCCATGCAGAAAGCATCCCTCACCCATCCTAGAGGCAGGCAGGAGCCCTTCTA
                                661                 681
701
TACCCACCCAGAATGAGACATCCAGCAGAGATTTCCAGCCTTCTACTGCTCTCCTCCACCTCAACTCCGTGC
        721                                 741                    761
781
TTAACCAAAGAAGCTGTACTCCGGGGGTCTCTTCTCTGAATAAAGCAATTAGCAAATCAAAAA
                  801            821
```

FIG. 4B

1:   TGCGTTTTGGGGGTTCCTGGAGTATCAATCATGGATCAAGAAACTGTAGGCAATGTGTCCTGTTGGCCATC
                                     MetAspGlnGluThrValGlyAsnValValLeuLeuAlaIle

73:  GTCACCCTCATCAGCGGTGGTCCAGAATGGATTCTTTGCCATAAAGTGGAGCACGAAAGCAGGACCCAGAAT
     ValThrLeuIleSerValValGlnAsnGlyPhePheAlaHisLysValGluHisGluSerArgThrGlnAsn

145: GGGAGGAGCTTCCAGAGGACCGGAACACTTGCCTTTGAGCGGGTCTACACTGCCAACCAGAACTGTGTAGAT
     GlyArgSerPheGlnArgThrGlyThrLeuAlaPheGluArgValTyrThrAlaAsnGlnAsnCysValAsp

217: GCGTACCCCACTTTCCTCGTCTGGGGCTACTTTGCAGCCAAGTTCCTGCGTTTGCT
     AlaTyrProThrPheLeuValLeuTrpSerAlaGlyLeuLeuCysSerGlnValProAlaAlaPheAla

289: GGACTGATGTACTTGTTTGTGCGGCAAAAGTACTTTGTGGTTACCTAGGAGAGAACGCAGAGACCACCCT
     GlyLeuMetTyrLeuPheValArgGlnLysTyrPheValGlyTyrLeuGlyGluArgThrGlnSerThrPro

361: GGCTACATATTGGGAAACGCATCATACTCTTCCTGTCCTCATGTCCGTTGCTGGCATATTCAACTATTAC
     GlyTyrIlePheGlyLysArgIleIleLeuPheLeuPheLeuMetSerValAlaGlyIleIlePheAsnTyrTyr

433: CTCATCTTCTTTTCGGAAGTGACTTTGAAAACTACATAAAGACGATTCCACCATCTCCCCTCTACTT
     LeuIlePhePhePheGlySerAspPheGluAsnTyrIleLysThrIleSerThrThrIleSerProLeuLeu

505: CTCATTCCTAACTCTCTGCTGAATATGGGTTGGT
     LeuIleSer***

FIGURE 5

```
  1: CTCTATCGACGAGTCTGGTAGCTGAGCGTTGGGCTGTAGTCGCTGTGTGTGATCCCCAGAGCCATGC
                                                                    MetP

73: CCGAGATAGTGGATACCTGTTCGTTGGCCTTCTCCGGCTTCCGTTCCGTCCGACCAAGCACCTGCGCT
     roGluIleValAspThrCysSerLeuAlaSerProAlaSerValCysArgThrLysHisLeuArgC

145: GCAGCGTCGACTTTACTCGCCCGGACGCTGACCGGGACTGTCTGCTCCAGGTCCAGTCTCAGGAGGACAATC
     ysSerValAspPheThrArgPheThrLeuProThrLeuProAlaAlaLeuThrValGlnSerGlnGluAspAsnL

217: TGCGCAGCCTGGTTTGGATACAAAGGACCTTACAATAGAAAAAGTAGTGATCAATGACAAGAAGTCAAAT
     euArgSerLeuValLeuAspThrLysAspLeuThrIleGluLysValValIleAsnGlyGlnGluValLysT

289: ATGCTCTTGGAGAAAGACAAAGTTACAAGGGATGCCAATGAAATCTCTCTTCCTATGCTTTGAGCAAAA
     yrAlaLeuGlyGluArgGlnSerTyrLysGlySerProMetGluIleSerLeuProIleAlaLeuSerLysA

361: ATCAAGAAATTGTTATAGAAATTCTTTTGAGACCCTCCAAAATCTTCTGCTCTCCAGTGCTCACTCCTG
     snGlnGluIleValIleGluIleIleSerPheGluThrSerProLysSerSerAlaLeuGlnTrpLeuThrProG

433: AACAGACTTCTGGGAAGGAACACCCATATCTCTTAGTCAGTGCCAGGCCCATCCACTGCAGAGCAATCCTTC
     luGlnThrSerGlyLysGluHisProTyrLeuPheSerGlnCysGlnAlaIleHisCysArgAlaIleLeuP

505: CTTGTCAGGACACTCCTTCTCTGAAATTAACCTATACTGAGAGGTGTCGTCCTAAAGAACTGGTGGCAC
     roCysGlnAspThrProSerValLysLeuThrTyrThrAlaGluValSerValProLysValGluValAlaL

577: TTATGAGTGCTATTCGTGATGGAGAAACACCTGACCCAAGCAGGAAGAAAATATACAAATTCATCC
     euMetSerAlaIleArgAspGlyGluThrProAspProSerArgLysIleTyrLysPheIleG

649: AAAAAGTTCCAATACCCTGCTACCTGATTGCTTTAGTTGTTGGAGCTTTAGAAAAGCAGGCAAATTGGCCCAA
     lnLysValProIleProCysTyrLeuIleAlaLeuValValGlyAlaLeuGluSerArgGlnIleGlyProA

721: GAACTTTGGTGTGCTCTGAGAAAGACAGTTGGAAAAGTCTGCTTATGAGTTTCTGAGACTGATCTATGC
     rgThrLeuValTrpSerGluLysGluGlnValGluLysSerAlaTyrGluPheSerGluThrGluSerMetL

793: TTAAAATAGCAGAAGATCTGGGAGGACCGTATGTATGGGACAGTGACCTATTGGTCCTGCCACATCCT
     euLysIleAlaGluAspLeuGlyGlyProTyrValTrpGlnTyrAspLeuLeuValLeuProSerP
```

FIG. 6A

```
 865: TCCCTTATGGTGGCATGGAGAATCCTTGCCTTACTTTTGTAACTCCTACTCTGCAGGGGACAAGTCAC
      heProTyrGlyGlyMetGluAsnProCysLeuThrPheValThrProThrLeuLeuAlaGlyLysAspLysSerL

937: TCTCCAATGTCATTGCACATGAAATCTCATAGCTGACAGGAATCTAGTGACCAACAAAACTTGGATC
      euSerAsnValIleAlaHisGluIleSerHisSerTrpPheGlyAsnLeuValThrAsnLysThrTrpAspH

1009: ACTTTGGTTAAATGAGGGACATACTGTGTACTTGGAACGCCACATTTGCGGACGATTGTTGGTGAAAAGT
      isPheTrpLeuAsnGluGlyHisThrValTyrLeuGluArgHisIleCysGlyArgLeuPheGlyGluLysP

1081: TCAGACATTTTAATGCTCTGGGAGGATGGGAGAACTACAGAATTCGGTAAAGACATTTGGGAGACACATC
      heArgHisPheAsnAlaLeuGlyGlyTrpGlyGluLeuGlnAsnSerValLysThrPheGlyGluThrHisP

1153: CTTTCACCAAACTGTGGTTGATCTGACAGATATAGACCCTGATGTAGCTTATTCTTCAGTTCCTATGAGA
      roPheThrLysLeuValValAspLeuThrAspIleAspProAspValAlaTyrSerSerValProTyrArgL

1225: AGGGCTTTGCTTTACTTTTTTACCTTGAACAACTGCTTGGAGGACCAGAGATTTTCCTAGGATTCTTAAAG
      ysGlyPheAlaLeuLeuPheTyrLeuGlnLeuLeuGlyLeuGlyProGluIlePheLeuGlyPheLeuLysA

1297: CTTATGTTGAGAAGTTTTCCTATAAGAGCATAACTACTGATGACTGGAAGGATTCCTGTATTCTATTTTA
      laTyrValGluLysPheSerTyrLysSerIleThrThrAspAspTrpLysAspPheLeuTyrSerTyrPheL

1369: AAGATAAGGTTGATGTTCTCAATCAAGTTGAATGCCCTGGCTCTACTCTCCTGGACTGCCTCCCATAA
      ysAspLysValAspValLeuAsnGlnValAspTrpAsnAlaTrpLeuTyrSerProGlyLeuProProIleL

1441: AGCCCAATTATGATATGACTCTGACAAATGCTTGTATTGCCTTAAGTCAAAGATGATTACTGCCAAGAAG
      ysProAsnTyrAspMetThrLeuThrAsnAlaCysIleAlaLeuSerGlnArgTrpIleThrAlaLysGluA

1513: ATGATTAAATTCATTCAATGCCACCTCTTCCATTGGGGCACATAAAGCCGAATGCAAGAGGTGTACAACTTCAATGCCA
      spAspLeuAsnSerPheAsnAlaThrArgAspLeuLysAspLeuSerSerHisGlnLeuAsnGluPheLeuAlaG

1585: AGACGCTCCAGAGGCCACCTCTTCCATTGGGGCACATAAAGCCGAATGCAAGAGGTGTACAACTTCAATGCCA
      lnThrLeuGlnArgAlaProLeuProLeuGlyHisIleLysArgMetGlnGluValTyrAsnPheAsnAlaI

1657: TTAACAATTCTGAAATACGATTCAGATGCCTCGCGTCTGCATTCAATCCAAGTGGGAGGAGGACGCAATTCCTT
      leAsnAsnSerGluIleIleArgPheArgTrpLeuArgLeuCysIleGlnSerLysTrpAlaIleProL
```

FIG. 6B

1729: TGGCGCTAAAGATGGCAACTGAACAAGGAAGAATGAAGTTTACCGGCCCTTATTCAAGGATCTTGCCT
      euAlaLeuLysMetAlaThrGluGlnGlyArgMetLysPheThrArgProLeuPheLysAspLeuAlaP

1801: TTGACAAATCCCATGATCAAGCTGTCCGAACCTACCAAGAGCACAAAGCAAGCATCCCGTGACTGCAA
      heAspLysSerHisAspGlnAlaValArgThrTyrGlnHisLysAlaSerMetHisProValThrAlaM

1873: TGCTGGTGGGGAAAGACTTAAAAGTGGATTAAAGACCTGCGTATTGATGATTTAGAGATTTCTCTTTTA
      etLeuValGlyLysAspLeuLysValAsp***

1945: AATGGAATTCGTAAAGAAATATAAAACTTCAGCTCACAATTAAAACTGTCTTTTTAGTTTTGGCTTTTATT

2017: GTTTTGTTGGTGATTTACTGAAATAAAGATGAGCTACTTCTTC

FIG. 6C

```
  1: GAATTCGGCCTGAGTGACCCGAGTCGGGACGGGCTGCGCGGGGACCCCGAGCCCAAACCCGGGGC

73: AGGCGGGCAGCTGTGCCCGGGGCACGGCCAGCTTCCTGATTCCTCCGATTCCTCCTTCCTCCCTAAAGC

145: GGCCGACAATGTCCACCACGGTCAATGTAGATTCCCTGGAATATGAGAAGACCCAGATCAAGAGAGCCC
                MetSerThrThrValAsnValAspSerLeuAlaGluTyrGluLysSerGlnIleLysArgAlaL

217: TGGAGCTGGGACGGTGATGACTGTGTTCAGCTTCCCAAGTCCACCCCGAGGAGAACCGTCCAGGTGA
     euGluLeuGlyThrValMetThrValPheSerPheArgLysSerThrProGluArgArgThrValGlnValI

289: TCATGGAGACGCGGCAGGTGGCCTGGACAAGACCGGACAAGATGAGGGCTTCTTGATATCATGGAAA
     leMetGluThrArgGlnValAlaTrpSerLysThrAlaAspLysIleGlyPheLeuAspIleMetGluI

361: TAAAAGAAATCCGCCAGGGAAGAACTCCAAAGATTCGAGCGAGCAAAAGCAGTTCGCCAGAAGAAGACT
     leLysGluIleArgProGlyLysAsnSerLysAspPheGluArgAlaLysAlaValArgGlnLysGluAspC

433: GCTGCTTCCACCATCCTATATGGCACTCAGTTCGTCCTCAGCACGTCCAGCTTGGCAGCTGACTCTAAAGAGG
     ysCysPheThrIleLeuTyrGlyThrGlnPheValLeuSerThrLeuSerLeuAlaAlaAspSerLysGluA

505: ATGCAGTTAACTGGCTCTCTGGCTTGAAAATCTTACACCAGGAAGCGATGAATGGCTCCACGCCCACCATTA
     spAlaAsnTrpLeuSerGlyLeuLysIleLeuHisGlnGluAlaMetAsnAlaSerThrProThrIleI

577: TCGAGAGTTGGCTGAGAAAGCAGATATATTCTGTGGATCAAACCAGAAGAAACAGCAGCATCAGTTCCGAGAGT
     leGluSerTrpLeuArgLysGlnIleTyrSerValAspThrArgArgAsnSerIleSerLeuArgGluL

649: TGAAGACCATCTGCCCCTGATCAACTTTAAAGTGAGCAGTGCCAAGTTCCTAAAGATAAGTTGTGAAA
     euLysThrIleLeuProLeuIleAsnPheLysValSerSerAlaLysPheLeuLysAspLysPheValGluI

721: TAGGAGCACACAAAGATGAGCTCAGCTTTGAACAGTTCCATCTCTTCATAAAAAACTTATGTTGAACAGC
     leGlyAlaHisLysAspGluLeuSerPheGluGlnPheHisLeuPheTyrLysLeuMetPheGluGlnG

793: AAAAATCGATTCTCGATGAATTCAAAAGGATTCGTCCGTGTTCATCCTGGGAACACTGACAGGCCGGATG
     lnLysSerIleLeuAspGluPheLysLysAspSerValPheIleLeuGlyAsnThrArgProAspA

865: CCTCTGCTGTTACCTGCATGACTTCCAGGTTTCTCATGAACAGCAGGAGCATTGGGCTCAGGATC
     laSerAlaValTyrLeuHisAspPheGlnArgPheLeuIleHisGluIleGlnGlnGluHisTrpAlaGlnAspL
```

FIG. 7A

937: TGAACAAAGTCCGTGAGCGATGACAAAGTTCATTGATGACACCATGCTGTGAAACTGCTGAGCCTTTCTGT
euAsnLysValArgGluArgMetThrLysPheIleAspAspThrMetArgGluThrAlaGluProPheLeuP

1009: TTGTGGATGAGTTCCTCACGTACCTGTTTCACGAGAAAACAGCATCTGGATGAGAAGTATGACGGGTGG
heValAspGluPheLeuThrTyrLeuPheSerArgGluAsnSerIleTrpAspGluLysTyrAspAlaValA

1081: ACATGCAGGACGATGAACAACCCCCTGTCTCATTACTGTCTTCCTCGTCACATAACACTACCTTACAGGTG
spMetGlnAspMetAsnAsnProLeuSerHisTyrTrpIleSerSerSerHisAsnThrTyrLeuThrGlyA

1153: ACCAGCTGCGGAGCTGTCCCCAGAAGCTACATCCGCTGCCTGCCATGGCTGTCGCTGCTGCATTGAAC
spGlnLeuArgSerGluSerProGluAlaTyrIleArgCysLeuArgMetGlyCysArgCysIleGluL

1225: TGGACTGCTGGGACGGGCCCGATGGAAGCCGTCATCTACCATGGCTGGACGGCTACCAAGATCAAGT
euAspCysTrpAspGlyProAspGlyLysProValIleTyrHisGlyTrpThrArgThrThrLysIleLysP

1297: TTGATGACGTCCTGCAGCTGAGCAACAGCGTCACAGCCTTGTTACCTGAGCTTCCCAGTGATCCTGTCCATCG
heAspAspValValGlnAlaSerSerValThrAlaLeuLeuLeuSerPheProValIleLeuSerIleG

1369: AGGAGCACTGCAGCTGGAGCAACAGCGTCACATGGCCAAGGCCTTCAAGGAAGTATTGGCGACCTGCTGT
luGluHisCysSerSerValGluGlnArgHisMetAlaLysAlaPheLysGluValPheGlyAspLeuLeuL

1441: TGACGAAGCCACGGACCCAGGCCAGTGCTGACCAGCTGCCCGCCAGCCAGGGACTCAAGGAGAAGATCATCA
euThrLysProThrGluProThrGlnAlaSerAlaAspGlnLeuProSerProSerGlnLeuArgLysIleIleIleL

1513: AGCATAAGAAGCTGGGCCCCCCGAGGCCGATGTGATGTCAACATGGAGGACAAGAAGGACGAACAAGCAAC
ysHisLysLysLeuGlyLeuGlyProArgGlyAspValAspValAsnMetGluAspLysLysAspGluHisLysGlnG

1585: AGGGGAGCTGTACATGTGGATTCCATTGACCAGAAATGACTGGCACTCTGCCATTGCTGATGCCA
lnGlyGluLeuTyrMetTrpAspSerIleAspGlnLysTrpThrArgHisTyrCysAlaIleAlaAspAlaL

1657: AGCTGTCCTTCAGTGACATTGAACAGACTATGGAGGAGAAGTGCCCAGATACCCCTACAGAAC
ysLeuSerPheSerAspAspIleGluGlnThrMetGluGluValProGlnAspIleProProThrGluL

1729: TACATTTGGGAGAAATGGTTCCACAAGAAGGTGGAGAAGAGGACCAGTGCCGAGAAGTTGCTGCTGCAGGAAT
euHisPheGlyGluLysTrpPheHisLysLysValGluGluArgThrSerArgThrAlaGluLysLeuLeuGlnGluT

FIG. 7B

```
1801: ACTGCATGGAGACGGGGGGCAAGGATGGCACCTTCCTGGTTCGGGAGAGCGAGACCTTCCCAATGACTACA
      yrCysMetGluThrGlyGlyLysAspGlyThrPheLeuValArgGluSerGluThrPheProAsnAspTyrT

1873: CCCTGTCCTTCTGGCGGTCAGGCCGGGTTCAGGCCGGTCCAGCACTGCCGGATCCGCTCCACCATGGAGGGGGGGACCCTGA
      hrLeuSerPheTrpArgSerGlyArgValGlnHisCysArgIleArgSerThrMetGluGlyGlyThrLeuL

1945: AATACTACTTGACTGACAACCTGAGGTTCAGGAGGATGTATGCCCTCATCCAGCACTACCGCGAGACGCACC
      ysTyrTyrLeuThrAspAsnLeuArgPheArgArgMetTyrAlaLeuIleGlnHisTyrArgGluThrHisL

2017: TGCCGTGCCGCAGTTCGAGCTCGCGGCTCGACGACCCTGCCCAACCCAACCCAGAGTCCAAGCCGT
      euProCysAlaGluPheGluLeuArgLeuThrAspProValProAsnProHisGluSerLysProT

2089: GGTACTATGACAGCCTGAGCCGCCGGAGCAGGACAGGACATGTGATGAGGATTCCCGGGACGGGGCCTTCC
      rpTyrTyrAspSerLeuSerArgGlyGluAlaGlyMetLeuMetArgIleProArgAspGlyAlaPheL

2161: TGATCCGGAAGCGAGAGGGAGGAGCGACTCCATGCCTAGGGCTAGGGCAAGGTAAAGCATTGTC
      euIleArgLysArgGluGlySerAspSerTyrAlaIleThrPheArgAlaArgGlyLysValLysHisCysA

2233: GCATCAACCGGACGGCCGACTTTGTGCTGGGGACCTCCGCTATTTGAGAGTCTGTGGAGCTCGTCA
      rgIleAsnArgAspGlyArgHisPheValLeuGlyThrSerAlaTyrPheGluSerLeuValGluLeuValS

2305: GTTACTACGAGAAGCATTCACTCTACCGAAAGATGAGACTGCCTACCCCCTGACCCCCGAGCTCCTGGAGC
      erTyrTyrGluLysHisSerLeuTyrArgLysMetArgLeuArgTyrProValThrProLeuLeuGluA

2377: GCTACAATACGAGAAAGAGATATAAACTCCCTCGACGTCAGCAGAATGTATGTGGATCCCAGTGAAATCA
      rgTyrAsnThrGluArgAspIleAsnSerLeuTyrAspValSerArgMetTyrValAspProSerGluIleA

2449: ATCCGTCCATGCCTCAGAGAACCGTGAAAGCTCTGTATGACTACAAAGCCAAGCGAAGCGATGAGCTGAGCT
      snProSerMetProGlnArgThrValLysAlaLeuTyrAspTyrLysAlaLysArgSerAspGluLeuSerP

2521: TCTGCCGTGGTGCCTCATCCACAATGTCTCCAAGGAGCCCGGGGCTGGTGAAAGGAGACTATGAACCA
      heCysArgGlyAlaLeuIleHisAsnValSerLysGluProGlyGlyTrpLysGlyTrpLysGlyTyrThrA

2593: GGATCCAGCAGTACTTCCCATCCAACTACGTCGAGGACATCTCAACTCGAGGAGCTAGAAAAGC
      rgIleGlnGlnTyrPheProSerAsnTyrValGluAspIleSerThrAlaAspPheGluGluLeuGluLysG
```

FIG. 7C

```
2665: AGATTATTGAAGACAATCCCTTAGGTCTCTCTTTGCAGAGGAATATTGACCTCAATACCTATAACGTCGTGA
      lnIleIleGluAspAsnProLeuGlySerLeuCysArgGlyIleLeuAspLeuAsnThrTyrAsnValVall 2737: AAGCCCCTCAGGGAAAAACCAGAAGTCCTTGTCTTCTTCATCCTGGACCCAAGGAGCAGGGCGATCCTCGG
      ysAlaProGlnGlyLysAsnGlnLysSerPheValPheLeuLeuGluGluProLysGluGlnGlyAspProV 2809: TGGAGTTTGCCACAGGGGTGGAGGAGTTCTTTGAGTGGTTTCAGAGCATCCAGAGATCACGTGGAAGA
      alGluPheAlaThrAspArgValGluGluLeuPheGluTrpPheGlnSerIleArgGluIleThrTrpLysI 2881: TTGACAGGAGAACAACATGAAGTACTGGAGAAGAACCAGTCCATCGCCATCGAGCTCTCTGACCTGG
      leAspSerLysGluAsnAsnMetLysTyrTrpGluLysAsnGlnSerIleAlaIleGluLeuSerAspLeuV 2953: TTGTCTACTGCAAACAACCAGCAAAACCAAGGACAACTTAGAAAATCCTGACTTCCGAGAAATCCGCTCCT
      alValTyrCysLysProThrSerLysThrLysAspAsnLeuGluAsnProAspPheArgGluIleArgSerP 3025: TTGTGGAGACGAAGGCTGACAGCATCATCAGACAGAAGCCCGTCGACCTCCTGAAGTACAATCAAAAGGCC
      heValGluThrLysAlaAspSerIleIleArgGlnLysProValAspLeuLeuLysTyrAsnGlnLysGlyL 3097: TGACCCGCGTCTACCCAAAGGGACAAAGAGTTGACTCTTCAAACTACGACCCCTTCCGCTTCCTGGCTGCG
      euThrArgValTyrProLysGlyGlnArgValAspSerSerAsnTyrAspProPheArgLeuTrpLeuCysG 3169: GTTCTCAGATGGTGGCACTCAATTTCCAGACGCAGATAAGTACATGCAGATGAATCACGATTGTTTCTC
      lySerGlnMetValAlaLeuAsnPheGlnThrAlaAspLysTyrMetGlnMetAsnHisAlaLeuPheSerL 3241: TCAACGGGCGCACGGGCTACGTTCTGCAGCATGAGGAGACAGAGAAATATGACCGATGCACCCG
      euAsnGlyArgThrGlyTyrValLeuGlnProGluSerMetArgThrGluLysTyrAspProMetProProG 3313: AGTCCCAGGAAGATCCTGATGACGTCAAGTTCTCGGTTCTGCAGTTCAAGGTTCTCGGTTGTGGCAAGTTGAC
      luSerGlnArgLysIleLeuMetThrLeuThrPheValLysValLeuGlyAlaArgHisLeuProLysLeuA 3385: GAAGTATTGCCTGCTCCCTTTGTAGAAGTGAGATCTGTGGAGCCCAGTATGCCAACAACAAGTTCAAGACGA
      rgSerIleAlaCysProPheValGluValGluIleCysGlyAlaGluTyrGlyAsnAsnLysPheLysThrT 3457: CGGTTGTGAATGATAATGCCCTCAGCCTATCTGGCTCCAACACAGGAGAAGGTGACATTGAAATTTATG
      hrValValAsnAspAsnAlaLeuSerProIleTrpAlaProThrGlnGluLysValThrPheGluIleTyrA
```

FIG. 7D

```
3529:  ACCCAAACCTGGCATTTCTGCGCTTTGTGGTTTATGAAGAAGATATGTTCAGGATCCCAACTTTCTGCTC
       spProAsnLeuAlaPheLeuArgPheValValTyrGluGluAspMetPheSerAspProAsnPheLeuAlaH

3601:  ATGCCACTTACCCCATTAAAGCAGTCAAATCAGGATTCAGGTCCGTTCCTGAAGAATGGGTACAGGGAGG
       isAlaThrTyrProIleLysAlaValLysSerGlyPheArgSerValProLeuLysAsnGlyTyrSerGluA

3673:  ACATAGAGCTGGCTTCCCTCCCCTGGTTTCTGTGAGATGCGGCCAGTCCTGGAGAGCGAAGAGGAACTTACT
       spIleGluLeuLeuAlaSerLeuLeuValPheCysGluMetArgProValLeuGluSerGluGluLeuTyrS

3745:  CCTCCTATCGCCAGCTGAGGAGGCGGCAAGAAGAACTGAACAACCAGCTCTTTCTGTATGACACACCAGA
       erSerTyrArgGlnLeuArgArgArgGlnGluGluLeuAsnAsnGlnLeuPheLeuTyrAspThrHisGlnA

3817:  ACTTGCGCAATGCCAACCGGGATGCCCTGGTTAAAGAGTTCAGTGTTAATGAGAACCACTCCAGCTGTACCA
       snLeuArgAsnAlaAsnArgAspAlaLeuValLysGluPheSerValAsnGluAsnHisSerSerCysThrA

3889:  GGAGAAATGCAACAAGAGGTTAAGAGAGAAGAGAGTCAGCAACAGCAAGTTTACTCATAGAAGCTGGGGTA
       rgArgAsnAlaThrArgGly***

3961:  TGTGTGTAAGGGTATTGTGTGTGTGCGCCATGTGTGTTGCATGTAGGAGAACGTGCCCTATTCACACTCTGG

4033:  GAAGACGCTAATCTGTGACATCTTTTCTTCAAGCCTGCCATCAAGGACATTTCTTAAGACCCAACTGGCATG

4105:  AGTTGGGGTAATTCCCTATTATTTCATCTTGGACAACTTCTAACTTATATCTTTATAGAGGATTCCCAAA

4177:  ATGTGCTCCTCATTTTTGCCCTCTCATGTTCCAAACCTCATTGAATAAAAAGCAATGAAAACCTTGAAAAAA

4249:  AAAAAAAAAAA
```

FIG. 7E

OLIGONUCLEOTIDE MODULATION OF ARACHIDONIC ACID METABOLISM

This application is a continuation of application Ser. No. 07/516,969, filed Apr. 30, 1990, now abandoned.

FIELD OF THE INVENTION

This invention relates to therapies, diagnostics, and research reagents for disease states which respond to modulation of the synthesis or metabolism of arachidonic acid. In particular, this invention relates to antisense oligonucleotide interactions with certain messenger ribonucleic acids or DNA involved in the synthesis of proteins regulating arachidonic acid synthesis or metabolism. These oligonucleotides have been found to lead to the modulation of the activity of the RNA or DNA, and thus to the modulation of the synthesis and metabolism of arachidonic acid. Palliation and therapeutic effect result.

BACKGROUND OF THE INVENTION

The Eicosanoids

Metabolites of arachidonic acid and related fatty acids exhibit a wide range of biological activities affecting every organ system in the body. There are over thirty metabolites of arachidonic acid which exhibit biological activity. These metabolites are collectively termed eicosanoids.

Arachidonic acid is stored in the cell esterified to membrane lipids. Once released from membrane lipids, arachidonic acid may either be re-esterified back into membrane lipids or metabolized via a variety of oxidative enzymes. There are two oxidative pathways which are of importance for therapeutic intervention; the cyclo-oxygenase pathway which generates prostaglandins, thromboxanes and prostacyclin, and the lipoxygenase pathway which generates leukotrienes, lipoxins, hydroperoxyeicosatetraenoic acids and the mono- and di-hydroxyeicosatetraenoic acids (mono- and di-HETE's). (See FIG. 1). Although platelet activating factor (PAF) is not a direct metabolite of arachidonic acid, it is generated through one of the pathways which generate free arachidonic acid. Thus, in some cases, generation of free arachidonic acid also results in the generation of lyso-PAF, a direct precursor for PAF.

Prostaglandins of the E series ($PGE_1$, $PGE_2$) are potent vasodilators and smooth muscle relaxants. Thus, $PGE_2$ promotes hypotension and relaxes bronchial, tracheal and uterine smooth muscle. Other effects of these prostaglandins include inhibition of platelet aggregation, inhibition of mediator release from mast cells, increased renal blood flow, diuresis, increased circulating concentrations of ACTH, and inhibition of gastric acid secretion. PGEs cause pain when injected intradermally and sensitize afferent nerve endings to the effects of chemicals or mechanical stimuli.

Prostaglandin D2, like PGE1, is an inhibitor of platelet aggregation. PGD2 enhances the release of histamine from basophils, promotes chemokinesis and enhances the chemotactic response of other mediators in polymorpholeukocytes. Prostacyclin ($PGI_2$) is a potent vasodilatory substance and, general smooth muscle relaxant. $PGI_2$ is 30 to 50 times more potent than PGE2 and PGD2 in inhibiting platelet aggregation. PGI2 inhibits gastric acid secretion, relaxes bronchial and uterine smooth muscle, and increases renal blood flow. Thus, PGE2, PGI2, and, to a lesser extent PGD2, are important in maintaining normal homeostasis and have beneficial effects in many clinical situations.

Prostaglandins of the F series, i.e., PGF2α, in general exhibit biological activity opposite to PGE on smooth muscle tissue. PGF2α contracts bronchial and tracheal smooth muscle, contracts both pregnant and nonpregnant uterine smooth muscle, and contracts gastrointestinal smooth muscle. In subprimates PGF2α is the leutolytic hormone.

Thromboxane $A_2$ ($TXA_2$) is a potent smooth muscle contractile agent, contracting all smooth muscle strips tested including vasculature, bronchial, and tracheal. $TXA_2$ promotes platelet aggregation and decreases renal blood flow.

In general, the peptidoleukotrienes (leukotrienes $C_4$, $D_4$, and $E_4$) are potent smooth muscle contractile agents, while leukotriene $B_4$ $(LTB_4)$ is a chemotactic factor for circulating neutrophils and monocytes. $LTB_4$ also promotes lysosomal enzyme release and superoxide anion generation from neutrophils, both of which cause local tissue damage (Ford-Hutchinson, A. W., *Crit. Rev. in Immunol.*, 10:1–12, 1989). Lipoxins have been shown to contract guinea pig parenchymal strips, inhibit natural killer cells, and to stimulate superoxide generation in neutrophils.

Platelet activating factor (PAF) induces platelet aggregation, increases vascular permeability, acts as a bronchoconstrictor, decreases renal blood flow, decreases mesenteric circulation, and is the most potent gastric ulcerogen yet described (Rosam et al., *Nature*, 319: 54–56, 1986). PAF activates inflammatory cells promoting neutrophil and eosinophil chemotaxis and degranulation (Braquet et al., *ISI Atlas of Science: Pharmacology*, 187–198, 1987).

PATHOPHYSIOLOGY OF THE EICOSANOIDS

Respiratory System

The effects of the leukotrienes on the respiratory system have been studied extensively because of the proposed role leukotrienes play in immediate type hypersensitivity reactions such as asthma. High levels of peptidoleukotrienes have been detected in nasal secretion and lung lavage fluids in patients suffering from asthma, allergic rhinitis, cystic fibrosis, and chronic bronchitis (Dahlen et al., *Proc. Natl. Acad. Sci. U.S.A.*, 80:1712–1716, 1983). Leukotrienes C4 and D4 are potent smooth muscle contractile agents, promoting bronchoconstriction in a variety of species, including humans (Dahlen et al., *Nature*, 288:484–486, 1980). Leukotrienes C4 and D4 (LTC4 and LTD4) are about equipotent in promoting bronchial constriction and about 1000-fold more potent than histamine (Dahlen et al., *Nature*, 288: 484–486, 1980; Sirois et al., *Prost. Leuk. Med.*, 7: 327–340, 1981). In general, LTC4 and LTD4 are more active in promoting contraction of peripheral airways rather than central airways. In guinea pig tracheal strips, LTE4 is about 10-fold less potent than LTC4 and LTD4. The bronchoconstriction produced by LTC4 and LTD4 are due to an interaction with specific cell surface receptors (Mong et al., *Eur. J. Pharmacol.*, 102: 1–11, 1984). It is still controversial whether distinct receptors exist for LTC4 and LTD4. Leukotriene E4 appears to act as a bronchoconstrictive agent by interactions with the LTD4 receptor. Leukotriene B4 produces relatively weak contractions of isolated trachea and lung parenchyma. The contractions elicited by LTB4 are blocked in part by inhibitors of cyclo-oxygenase suggesting that the contraction are secondary to the release of prostaglandins.

Like the peptidoleukotrienes, platelet activating factor is a potent bronchoconstrictive agent. In addition, PAF induces an increase in airway reactivity to other agents in humans which may last up to 7 days following inhalation (Cuss et al., *Lancet,* 2: 189, 1986). The prostanoids PGF2α and TXA$_2$ also contract airway smooth muscle and have been implicated as contributory to the asthmatic response.

Cardiovascular System

Leukotrienes also act as vasoconstrictors, however, marked differences exist for different vascular beds. LTC4 and LTD4 are potent constrictors of coronary arteries in a variety of species (Roth and Leffer, *Prostaglandins,* 26: 573–581, 1983; Burke et al., *J. Pharmacol. Exper. Therap.,* 221:235–241, 1982; Letts and Piper, Br. *J. Pharmacol.,* 76: 169–176, 1982). As in the lung, LTE4 is about 10-fold less potent than LTC4 and LTD4, while LTB4 is without activity. In humans, LTC4 and LTD4 are potent contractile agents for pulmonary vein and weak contractants of pulmonary artery (Schellenberg and Foster, *Prostaglandins,* 27: 475–482, 1984). Intravenous injection of 2 nmol LTC4 into normal, healthy human volunteers produced a fall in mean arterial pressure, an increase in heart rate, a decrease in coronary blood flow and an increase in coronary vascular resistance (Marone et al., in *Biology of the Leukotrienes,* ed. by R. Levi and R. D. Krell, Ann. New York Acad. Sci. 524, New York Academy of Sciences, N.Y., pp. 321–333, 1988). Similar effects were reported for LTD4. LTC4 and LTD4 directly increase vascular permeability probably by promoting retraction of capillary endothelial cells.

There is increasing evidence which suggests that leukotrienes contribute to cardiac reperfusion injury following myocardial ischemia (Barst and Mullane, Eur. *J. Pharmacol.,* 114: 383–387, 1985; Sasaki et al., *Cardiovasc. Res.,* 22: 142–148, 1988). In experimental models of cardiac reperfusion injury, dual cyclo-oxygenase/lipoxygenase inhibitors have been shown to reduce the myocardial infarct size. The available evidence suggests that the beneficial effect of the dual inhibitors is by inhibition of LTB4 biosynthesis. However, these data must be interpreted cautiously as the compounds used in the studies inhibited both cyclo-oxygenase and lipoxygenases, in addition to having inherent anti-oxidant properties. Specific inhibitors of 5-LO or LTB4 antagonists are needed to verify these findings. Leukotrienes are also implicated as pathological mediators in endotoxic shock, in that selective LTD4 receptor antagonist significantly increase survival in animal models (Smith et al., *Circ. Shock,* 25: 21–31, 1988). The beneficial effects of LTD4 antagonists in endotoxic shock models may be due in part by their ability to reverse the increased capillary permeability caused by LTD4.

Platelet activating factor and thromboxane A$_2$ constrict coronary blood vessels thus decreasing coronary perfusion; the net result being impaired cardiac output, a decrease in blood pressure and acute circulatory collapse. PAF also promotes ST-segment depression. In experimental animal models of shock, there is a relationship between endotoxin-induced hypotension and the level of PAF. Further support for a role of PAF in endotoxic shock was the finding that PAF antagonists decrease the hypotension observed in animal models of shock (Braquet et al., ISY *Atlas of Science: Pharmacology;* 187–198, 1987).

Gastrointestinal System

The guinea pig ileum is the classical tissue to measure smooth muscle contraction by the peptido-leukotrienes (SRS-A). In addition, LTC4 and LTD4 contract guinea pig stomach. LTB4 is without effect on both tissues. There are marked differences between species and muscle layers in their responsiveness to leukotrienes. Human gastrointestinal mucosa synthesize and release leukotrienes, which is increased in response to injury or an inflammatory reaction. In experimental animal models, leukotriene receptor antagonists have been reported to decrease the gastrointestinal damage caused by ethanol, indomethacin, and aspirin. The gastrointestinal damage caused by leukotrienes may be due in part to their potent vasoconstrictive properties, thus shunting blood flow away from mucosa. Several studies have demonstrated elevations of LTB4 and the peptidoleukotrienes in patients suffering from inflammatory bowel disease. In animal models of inflammatory bowel disease, 5-LO inhibitors decrease the amount of damage and inflammation.

As already mentioned, PAF is the most potent ulcerogen in the rat yet described. PAF is also proposed to be involved in necrotizing enterocolitis (Wallace et al., *Gastroenterology,* 1987 in press).

Central Nervous System

Leukotrienes are synthesized and released from normal brain tissue stimulated with calcium ionophore, suggesting that they may function as neuromodulators. LTC4 and LTD4 produce prolonged excitation of cerebellar purkinje cells (Palmer etal., *J. Pharmacol. Exp. Ther.,* 219:91–96, 1981). In addition to a possible role as a neuromodulator, leukotrienes may contribute to pathology of nervous tissue following injury such as cerebral ischemia since they are potent constrictors of cerebral blood vessels. LTB4, LTC4, and LTD4 decrease the blood brain barrier by increasing vascular permeability, with LTB4 being the most potent (Black, *Prostaglandins Leukotriene Med.,* 14: 339–340, 1984).

Prostaglandins contribute to the pain associated with injury, inflammation, and headache, thus explaining the therapeutic benefit of nonsteroidal anti-inflammatory agents in these diseases. At lower doses, prostaglandins E2 and PGF2$^-$ sensitize pain receptors to mechanical and chemical stimulation producing a hyperalgesia.

Cutaneous System

Leukotrienes produce marked inflammatory responses in human skin. Injection of 0.15 to 1.5 nmol of LTB4 into human skin caused raised edematous areas which appeared 30 minutes after injection and lasted for at least 4 hours. Histology demonstrated a marked polymorphonuclear leukocyte infiltrate into the dermis (Camp etal., *Br. J. Pharmacol.,* 80: 497–502, 1983). Topical application of as little as 5 ng of LTB4 produced a delayed inflammatory reaction which first appeared at 12 hours and lasted for several days. Initially, the infiltrate consisted of polymorphonuclear leukocytes, but mononuclear leukocytes predominated at the later stages of the inflammatory reaction. Tachyphylaxis develops in response to repeated topical administration of LTB4 (Dowd et al., 1987).

In contrast to LTB4, the peptidoleukotrienes produce an immediate flair reaction upon intradermal injection, with no later sequelae. Some of the best evidence for the involvement of leukotrienes in a human disease is in psoriasis. Leukotrienes have been found in psoriatic lesions. Benoxaprofen, a 5-lipoxygenase inhibitor, was found to be effective in patients with severe psoriasis who did not respond to standard therapy (Kragballe and Herlin, *Arch. Dermatol.,* 119: 548–552, 1983). However, benoxaprofen was withdrawn from the market due to unacceptable side effects.

Prostaglandins E1 and E2 cause vasodilation and whealing when injected into the skin Crunkhorn and Willis, *Br. J. Pharmacol.*, 41: 49–56, 1971). Prostacyclin (PGI2) increases vascular permeability due to other mediators. Prostaglandin D2 is much weaker than PGE's in promoting redness and whealing following intradermal injection.

PAF is a potent pro-inflammatory agent in human skin. Injection of picomole amounts of PAF into human skin promotes a biphasic response with the early response ocurring 5 minutes after injection followed 3–6 hours later by a late phase response (Archer et al., *Br. J. Dermatol.*, 112:285–290, 1985). PAF has been isolated from scale and chamber fluid from lesional skin of patients with psoriasis (Mallet et al., *Adv. in Prostaglandins, Thromboxanes, Leukotrienes and Related Compounds*, Vol 17B: 640–642, 1987).

Musco-Skeletal System

High levels of leukotrienes and monohydroxy derivatives of arachidonic acid have been detected in synovial fluid from patients with rheumatoid arthritis, spondylarthritis, and gout (Klickstein et al., *J. Clin. Invest.*, 66: 1166–1170, 1950; Davidson et al., *Ann. Rheum. Dis.*, 42:677–679, 1983). The high levels of lipoxygenase products in synovial fluid may contribute to neutrophil infiltration and increased enzyme release from activated neutrophil into the synovial cavity, Inhibitors of 5-lipoxygenase have been shown to reduce tissue damage in collagen-induced arthritis in rodents, Inhibition of leukotriene biosynthesis reduces neutrophil and monocyte infiltration into the synovial space and the resultant tissue damage caused by these cells.

Current Therapeutic Agents Modulating Lipid Metabolism

It is evident by the wide variety of effects of eicosanoids on the major organ systems of the body and their association in a variety of pathological conditions that inhibitors of the metabolism of arachidonic acid would have immense therapeutic utility. Currently there are several classes of agents on the market which modulate arachidonic acid metabolism. However, with each class there a number of untoward effects due to their lack of specificity. In addition, most of the agents currently on the market fail to inhibit either the lipoxygenase pathway or platelet activating factor.

Inhibition of the enzyme, cyclo-oxygenase, by aspirin, ibuprofen, naproxen, indomethacin and related nonsteroidal analgesics has been well documented to exert beneficial effects in a variety of disease states. Nonsteroidal anti-inflammatory agents are the mainstay for the treatment of rheumatoid arthritis. These agents have proven very effective in relieving the symptoms associated with rheumatoid arthritis such as pain and swelling, however, they do little to alter the course of the disease. In addition, inhibitors of cyclo-oxygenase nondiscriminantly block production of all prostaglandins, some of which exert beneficial effects. This may in part be the mechanism for many of their side effects, such as their ulcerogenic activity. Cyclo-oxygenase inhibitors have no effect on either leukotriene-production or platelet activating factor, thus leaving a void in the therapy of a variety of diseases.

Steroids exhibiting glucocorticoid activity also exhibit anti-inflammatory activity, possibly by inhibiting the release of arachidonic acid from cell membranes. Steroids constitute one of the most widely prescribed classes of agents currently available. They are used to treat a variety of inflammatory, allergic, and nonimmune mediated disorders such as rheumatoid arthritis, osteoarthritis, lupus, anaphylaxis, urticaria, contact dermatitis, asthma, psoriasis, chronic ulcerative colitis, cerebral edema, septic shock, malignancies, and hepatitis. With the exception of substitution therapy for the treatment of adrenal insufficiency, glucocorticoid therapy is not curative. In addition, long term treatment with glucocorticoid leads to substantial and often life threatening side effects. As many of the uses of glucocorticoids are for the treatment of chronic disorders, their side effects limit their usefulness.

Changes in dietary intake of essential fatty acid precursors to arachidonic acid have demonstrated modest activity in inflammatory and cardiovascular diseases (Bonaa et al., *New Eng. J. Med.*, 322 795–801, 1990; Rangi et al., *J. Allergy Clin. Immunol.*, 85:484–489, 1990). Fish oils contain eicosapentaenoic acid (EPA), which is a poor substrate for cyclo-oxygenase and acts as a competitive inhibitor of cyclo-oxygenase. EPA is metabolized similar to arachidonic acid by lipoxygenases, but give much less active metabolites (Terano et al., *Biochem. Pharmacol.*, 33:3071–3076, 1984). Thus, EPA competes with arachidonic acid for incorporation into cellular membranes and subsequent metabolism by lipoxygenases. It is difficult to completely restrict dietary intact of linoleic, linolenic and arachidonic acids thus limiting the usefulness of fish oil therapies.

Inhibition of 5-lipcoxygenase by an iron complexing reagent, a hydroxamic acid derivative, is currently undergoing clinical trials. Historically, this approach has yielded less than promising results. To date, no current agents for modulation of the storage or release of arachidonic acid from cellular membranes nor metabolism via the lipoxygenase pathways have proven to be useful therapeutic agents. There is a great, but as yet unfulfilled, need to provide a safe and efficacious method to modulate arachidonic acid synthesis or metabolism. A means to modulate the production of proteins at critical points in the arachidonic acid pathway, rather than seeking to inhibit specific enzymes directly, would overcome the problems encountered by prior workers.

OBJECTS OF THE INVENTION

It is a principal object of the invention to provide therapies for immunological, cardiovascular, and other diseases through perturbations in the synthesis or metabolism of arachidonic acid and related compounds.

It is a further object of the invention to provide antisense oligonucleotides which are capable of inhibiting the function of RNA encoding proteins involved in the synthesis and metabolism of arachidonic acid and related compounds.

Yet another object is to provide means .for diagnosis of dysfunctions of arachidonic acid synthesis or metabolism.

These and other objects of this invention will become apparent from a review of the instant specification.

BRIEF DESCRIPTION OF THE DRAWINGS

FIG. 3 is a human 5-lipoxygenase mRNA sequence.

FIG. 4 is a human synovial fluid PLA$_2$ mRNA sequence.

FIG. 5 is a human 5-lipoxygenase activating protein sequence.

FIG. 6 is a human LTA$_4$ hydrolase mRNA sequence.

FIG. 7 is a human phosphoinositde-specific phospholipase C mRN sequence.

SUMMARY OF THE INVENTION

Figure 1:
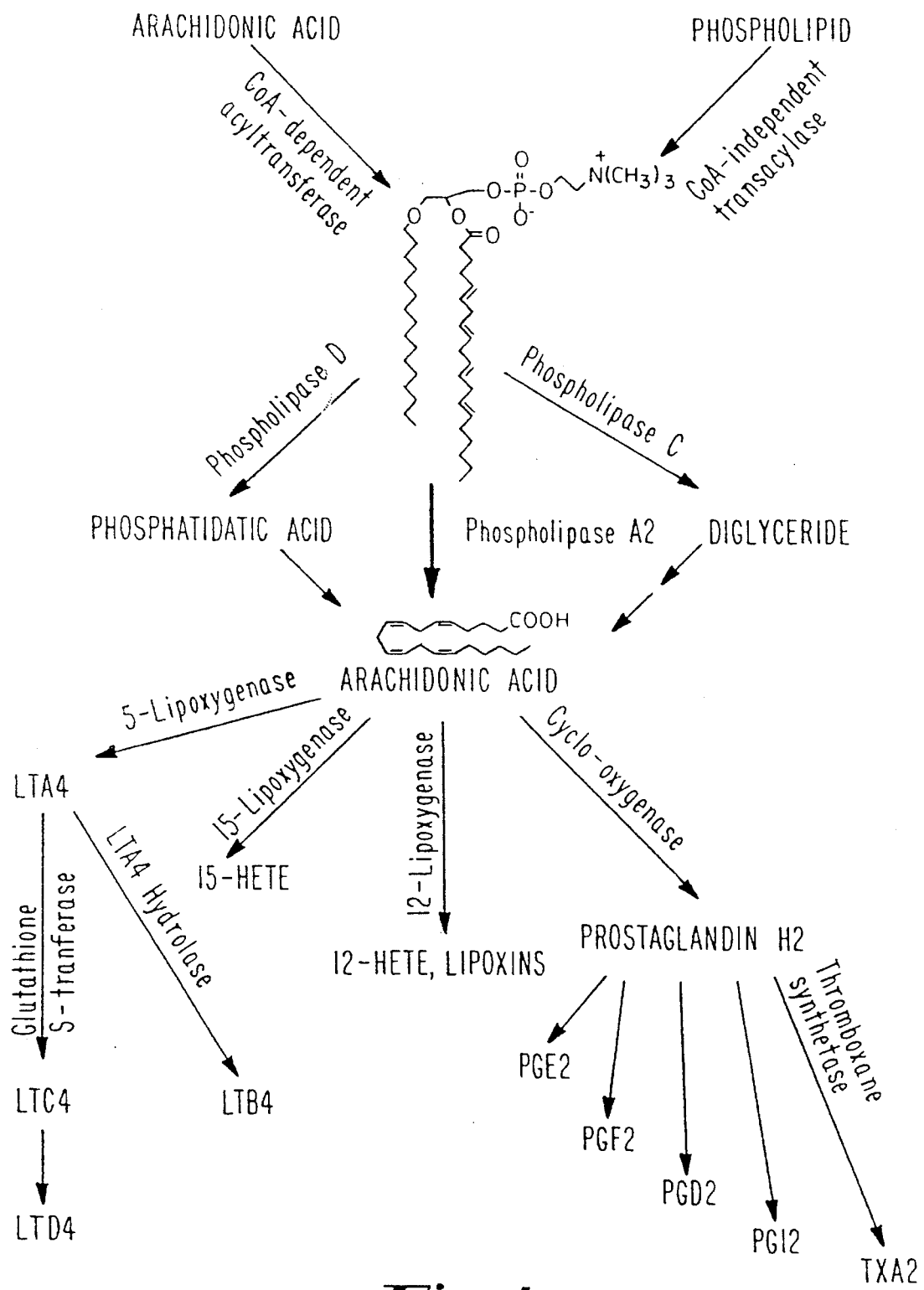
FIG. 1 is a schematic of the synthesis and metabolism of arachidonic acid.

In accordance with the present invention, oligonucleotides and oligonucleotide analogs are provided which specifically hybridize with nucleic acids encoding 5-lipoxygenase, a 5-lipoxygenase activating protein (FLAP), phospholipase A$_2$, Phospholipase C, LTA$_4$ hydrolase, and other proteins regulating lipid metabolism. The oligonucleotide or oligonucleotide analog is designed to bind directly to mRNA or to a selected gene forming a triple stranded structure, thereby modulating the amount of mRNA made from the gene.

The former relationship is commonly denominated as "antisense". The oligonucleotides and oligonucleotide analogs are able to inhibit the function of RNA or DNA, either its translation into protein, its translocation into the cytoplasm, or any other activity necessary to its overall biological function. The failure of the RNA or DNA to perform all or part of its function results in failure of a portion of the genome controlling arachidonic metabolism to be properly expressed, thus modulating said metabolism.

It is preferred to target specific genes for antisense attack. It has been discovered that the genes coding for a 5-lipoxygenase, 5-lipoxygenase activating protein, phospholipase A$_2$, LTA$_4$ hydrolase, phospholipase C, and coenzyme A-independent transacylase are particularly useful for this approach.

Methods of modulating arachidonic acid metabolism comprising contacting the animal with an oligonucleotide or oligonucleotide analog hybridizable with nucleic acids encoding a protein capable of modulating arachidonic acid synthesis or metabolism are provided. Oligonucleotides or analogs hybridizable with RNA or DNA coding for a 5-lipoxygenase, 5-lipoxygenase activating protein, phospholipase A$_2$, LTA$_4$ hydrolase, phospholipase C, thromboxane synthetase and coenzyme A independent transacylase are preferred.

DETAILED DESCRIPTION OF THE INVENTION

Antisense oligonucleotides hold great promise as therapeutic agents for the treatment of many human diseases. Conceptually, it is much easier to design compounds which interact with a primary structure such as an RNA molecule by base pairing than it is to design a molecule to interact with the active site of an enzyme. Oligonucleotides specifically bind to the complementary sequence of either pre-mRNA or mature mRNA, as defined by Watson-Crick base pairing, inhibiting the flow of genetic information from DNA to protein. The properties of antisense oligonucleotides which make them specific for their target sequence also makes them extraordinarily versatile. Because antisense oligonucleotides are long chains of four monomeric units, they may be readily synthesized for any target RNA sequence. Numerous recent studies have documented the utility of antisense oligonucleotides as biochemical tools for studying target proteins (Rothenberg et al., *J. Natl. Cancer Inst.*, 81:1539–1544, 1989; Zon, G., *Pharmaceutical Res.*, 5:539–549). Because of recent advances in oligonucleotide chemistry, synthesis of nuclease resistant oligonucleotides, and oligonucleotide analogs which exhibit enhanced cell uptake, it is now possible to consider the use of antisense oligonucleotides as a novel form of therapeutics.

Antisense oligonucleotides offer an ideal solution to the problems encountered in prior art approaches. They can be designed to selectively inhibit a given isoenzyme, they inhibit the production of the enzyme, and they avoid non-specific mechanisms such as free radical scavenging. A complete understanding of enzyme mechanism is not needed to design specific inhibitors.

Current agents which modulate the metabolism of arachidonic acid exhibit many unacceptable side effects due to their lack of specificity, or they exhibit only limited effectiveness in treating the disease. The instant invention circumvents problems encountered by prior workers by inhibiting the production of the enzyme, rather than inhibiting the enzyme directly, to achieve the therapeutic effect. There are many enzymes involved in the synthesis or metabolism of arachidonic acid which are of interest. Of these many enzymes, six have been selected as the most critical targets based upon their key role in arachidonic acid synthesis or their selectivity in the generation of specific arachidonic acid metabolites. As shown in FIG. 1, we have identified a number of proteins at key points in the arachidonic acid pathway. In the instant invention, the oligonucleotides or oligonucleotide analog is designed to bind directly to mRNA or to a gene forming a triple stranded structure which modulates the amount of mRNA made from the gene.

Arachidonic acid is an essential fatty acid which must be obtained from the diet either directly or by dietary intake of linoleic or linolenic acids, both of which may be metabolized to arachidonic acid in mammalian tissues. Arachidonic acid is stored esterified to membrane lipids. These include the neutral lipids such as triglycerides and diglycerides; phospholipids such as phosphatidylcholine, phosphatidylethanolamine, phosphatidylinositol, and phosphatidylserine; and cholesterol esters. Esterified arachidonic acid is not available for metabolism by the cyclo-oxygenase and lipoxygenase pathways. Thus, the rate limiting step for the synthesis of prostaglandins and leukotrienes is release from cellular membranes. In most mammalian cells, the major source of arachidonic acid for prostaglandin and leukotriene synthesis appears to be phospholipids. Cells stimulated with specific agonists release arachidonic acid from membrane phospholipids via a number of distinct pathways (FIG. 1). In a given tissue type all pathways may be operational, however, the most direct route for generation of free arachidonic acid, i.e., phospholipase A$_2$, appears to account for the greatest mass of arachidonic acid released. In some cell types, the phospholipase C/diglyceride lipase pathway may contribute significantly to the mass of arachidonic acid released from membrane lipids (Bell et al., *Proc. Natl. Acad. Sci. U.S.A.*, 76: 3238–3241; Mahadevappa and Holub, *Biochem. Biophys. Res. Comm.*, 134: 1327–1333, 1986).

Figure 2:
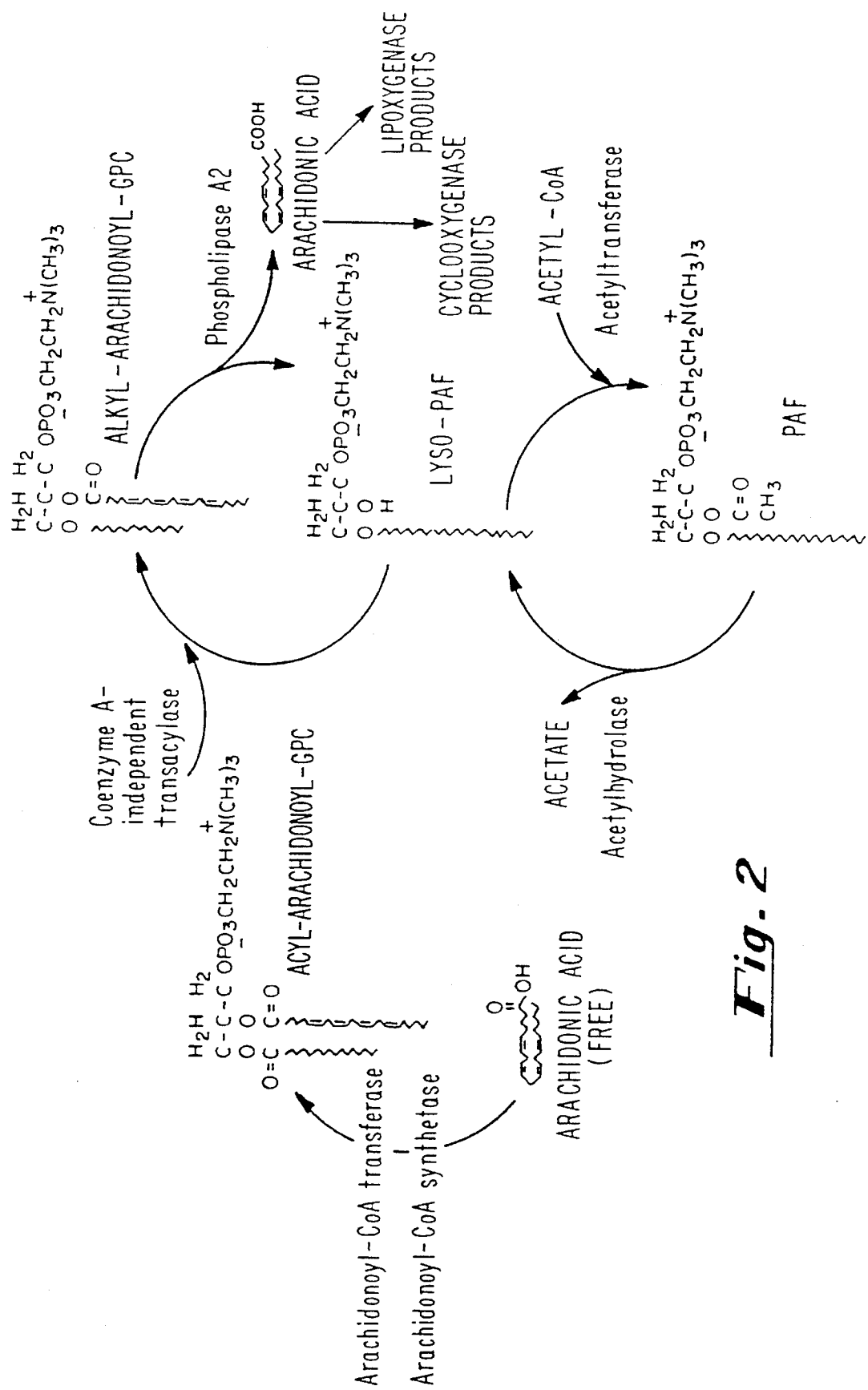
FIG. 2 is a schematic of the pathway for platelet activating factor synthesis.

Several recent studies suggest that the phospholipid pool from which arachidonic acid is released is different for the cyclo-oxygenase and lipoxygenase pathways (Humes et al., *J. Biol. Chem.*, 257:1591–1594; Chilton and Connell, *J. Biol. Chem.*, 263: 5260–5265, 1988; Skerrett et al., *J. Immunol.*, 144: 1052–1061, 1990). Thus, modulating distinct lipid pools may have different effects on the synthesis of prostaglandins and leukotrienes. In particular, a distinct subspecies of phosphatidylcholine with an ether linkage at position 1 (1-O-Alkyl, 2-arachidonyl phosphatiydylcholine) appears to be the major source of arachidonic acid used for $LTB_4$ synthesis in human neutrophils (Chilton and Connel, *J. Biol. Chem.*, 263: 5260–5265). Hydrolysis of this lipid species by a phospholipase $A_2$ results in free arachidonic acid and 1-O-Alkyl lysophosphatidylcholine, a direct precursor for platelet activating factor (FIG. 2). Inhibition of either the synthesis of this lipid species through inhibition of coenzyme A-independent transacylase or inhibition of the hydrolysis of the lipid through inhibition of phospholipase $A_2$ would inhibit both the production of leukotrienes and platelet activating factor.

Arachidonic acid released from membrane lipids may be re-esterified back into the lipids by an acyltransferase or further metabolized by a variety of oxygenases. Therapeutically, the two most important classes of oxygenases are cyclo-oxygenase and the lipoxygenases. Cyclo-oxygenase oxygenates and cyclizes arachidonic acid forming the cyclic endoperoxide intermediate PGH2, the first step in the synthesis of the prostaglandins (FIG. 1). There are multiple lipoxygenase enzymes in mammalian cells which are classified according to the position of the double bond in which they insert molecular oxygen, i.e., 5-lipoxygenase, 12-lipoxygenase, and 15-lipoxygenase. Although 12- and 15-lipoxygenase products have some biological activity, the best characterized lipoxygenase products are those derived from 5-lipoxygenase. The 5-lipoxygenase products, the leukotrienes, have potent biological activity and are implicated in contributing to the pathology in a variety of disease states. As part of the activation mechanism for 5-lipoxygenase, the enzyme apparently undergoes a calcium-induced translocation from the cytosolic fraction to the membrane where it interacts with a specific membrane protein termed 5-lipoxygenase activating protein (FLAP). The interaction of 5-lipoxygenase with FLAP appears to be obligatory for leukotriene synthesis in cells (Rouzer et al., *J. Biol. Chem.*, 265: 1436–1442; Dixon et al., *Nature*, 343: 282–284).

The identified antisense oligonucleotide targets are 5-lipoxygenase, 5-lipoxygenaee activating protein, specific isoenzymes of phospholipase C, specific isoenzymes of phospholipase $A_2$, $LTA_4$ hydrolase, and coenzyme A-independent transacylase. These targets represent several important subpathway approaches to arachidonic acid metabolism. The lipoxygenase pathway and platelet activating factor synthesis are approached by either inhibiting the synthesis of the precursor phospholipid 1-O-Alkyl, 2-arachidonyl phosphatidylcholine (coenzyme A-independent transacylase) or the release of arachidonic acid from the membrane phospholipids (phospholipase $A_2$ and phospholipase C). The lipoxygenase pathway may also be specifically blocked by inhibiting the metabolism of arachidonic acid into leukotrienes (5-lipoxygenase and $LTA_4$ hydrolase), or the activation of 5-lipoxygenase (5-lipoxygenase activating protein).

As can be seen by the selection of the targeted points, the means of modulation of arachidonic acid metabolism is dependent upon the protein selected.

DESCRIPTION OF TARGETS

Lipoxygenases are a family of dioxygenases which incorporate one molecule of oxygen into unsaturated fatty acids. Lipoxygenases maybe classified by the oxygenation site in the substrate molecule. 5-lipoxygenase (5-LO) is a dioxygenase which incorporates one oxygen molecule at the C5-double bond of arachidonic acid producing 5-hydroperoxy-6,8,11,14-eicosatetraenoic acid (5-HPETE). Purified 5-LO also converts 5-HPETE to a conjugated triene epoxide 5,6-leukotriene $A_4$. Thus, the first two enzymatic steps in leukotriene $B_4$ and the peptidoleukotrienes (leukotriene $C_4$, leukotriene $D_4$, and leukotriene $E_4$) biosynthetic pathways are performed by a single enzyme.

5-lipoxygenase (5-LO) has been purified to homogeneity from the cytosolic fraction of a number of cell types (Rouzer and Samuelsson, *Proc. Natl. Acad. Sci. U.S.A.*, 82:6040–6044, 1985; Hogaboom et al., *Mol. Pharmacol.*, 30:510–519, 1986; Ueda et al., *J. Biol. Chem.*, 261: 7982–7988,1986). The purified enzyme exhibits a molecular weight of 74 to 80 kDa as determined by SDS. polyacrylamide gel electrophoresis. 5-Lipoxygenase is a suicide enzyme, in that it inactivates itself in an irreversible manner during the course of the enzyme reaction. The exact mechanism by which 5-LO inactivates itself has not been elucidated. 5-LO can use both arachidonic acid and 5-HEPTE as substrates to synthesize $LTA_4$. With rat basophil 5-LO, exogenous 5-HPETE is about 50-fold less active as a substrate for $LTA_4$ synthesis than 5-HPETE supplied by the enzymes from the 5-lipoxygenase reaction.

The purified enzyme is activated by both calcium and ATP, as well as several unknown cellular factors which are removed from the enzyme during purification (Rouzer et al., *Proc. Natl. Acad. Sci. USA*, 82: 7505–7509, 1985; Hogaboom et al., *Mol. Pharm.*, 30:510–519, 1986). Both ATP and the stimulatory factors increase the initial velocity of the enzyme without exerting a stabilization effect towards the enzyme. Stimulation by ATP does not appear to involve protein phosphorylation nor does hydrolysis of the phosphodiester bond appear to be a requirement as ADP and AMP also stimulate. One mechanism by which calcium activates 5-LO is to promote the binding of 5-LO to cellular membranes (Rouzer and Samuelsson, *Proc. Natl. Acad. Sci. USA*, 84:7393–7397, 1987; Wong et al., *Biochemistry*, 27:6763–6769, 1988). Most agonists which promote leukotriene biosynthesis cause an increase in intracellular calcium, thus the translocation of 5-LO from the cytosol to cellular membranes may be an important regulatory event in leukotriene biosynthesis. This hypothesis is further supported by the observation that treatment of cells with calcium ionophore causes a translocation of 5-LO to the membrane with a concomitant production of leukotrienes (Rouzer and Kargman, *J. Biol. Chem.*, 263:10980–10988, 1988).

The cDNA and genomic clones for human 5-lipoxygenase (Dixon et al., *Proc. Natl. Acad. Sci. USA*, 85:416–420, 1988; Matsumoto et al., *Proc. Natl. Acad. Sci. USA*, 85:26–30, 1988; Funk et al., *Proc. Natl. Acad. Sci. USA*, 86:2587–2591, 1989) and the cDNA sequence and predicted protein sequence for rat 5-LO have been published (Balcarek et al., *J. Biol. Chem.*, 263:13937–11941, 1988). We have isolated and partially sequenced the rat genomic clone for 5-LO. The message for 5-LO is about 2700 bases in length. Human 5-LO is 674 amino acids in length with a calculated molecular weight of 77,839, while rat 5-LO is 670 amino acids in length. The protein sequence for human and rat 5-LO were 93% identical, while the cDNA sequences were over 80% identical. The major transcription initiation start site is 65 bp upstream from the AUG translation initiation colon. Human 5-LO mRNA contains 434 bp of 3'-nontranslated sequence prior to the polyadenylation site. 5-LO contains 2 domains which show 50- to 60% homology to the 17 amino acid consensus sequence for calcium-dependent membrane binding proteins such as lipocortin. The similarities between 5-LO and the calcium-dependent membrane binding proteins may explain the calcium-dependent translocation of 5-LO from the cytosol to membranes.

The human 5-LO gene is over 80,000 bases in length. The gene contains 14 exons and 13 introns which range in size from 192 base pairs (bp) to over 26 kb, which makes it among the largest genes known. The 5-LO gene appears to be a single copy gene. The 5-LO gene contains no TATA or CCAAT sequences in close proximity to the transcription initiation start site, a feature shared by several housekeeping genes. The putative promoter region does contain 8 sites for binding to the Sp1 transcription factor.

As discussed above, since 5-LO is involved in the biosynthetic pathways leading to leukotriene $A_4$, leukotriene $B_4$, and the peptidoleukotrienes, inhibition of 5-LO could be useful for modulating arachidonic acid metabolism. Certain antisense oligonucleotides and oligonacleotide analogs may be identified as useful for this purpose.

As indicated above 5-lipoxygenase requires a membrane factor for the synthesis of leukotrienes (Rouzer and Samuelsson, *Proc. Natl. Acad. Sci. USA*, 82:6040–6044). The identification of a novel leukotriene biosynthesis inhibitor which had no direct effects on 5-lipoxygenase, MK886, lead to the identification of an 18 kDa membrane protein which activates 5-lipoxygenase called 5-lipoxygenase activating protein (FLAP) (Miller et al., *Nature*, 343:276–281, 1990; Rouzer et al., *J. Biol. Chem.*, 265: 1436–1442, 1990). The cDNA for FLAP encodes for a 161 amino acid protein with a high content of hydrophobic amino acids (FIG. 3) (Dixon et al., *Nature*, 343:282–284, 1990). The mRNA for FLAP is 1 kb in length.

Several experiments demonstrate that FLAP is obligatory for leukotriene synthesis in intact cells. Osteosarcoma cells transfected with the 5-lipoxygenase cDNA express 5-lipoxygenase enzymatic activity but do not synthesize leukotrienes when stimulated with calcium ionophore. However, cells transfected with both 5-lipoxygenase and FLAP cDNA's express 5-lipoxygenase enzyme activity and produce leukotrienes following stimulation with calcium ionophore (Dixon et al., *Nature*, 343:282–284). Secondly, it was shown that MK886 can prevent translocation of 5-lipoxygenase from the cytosol to the membrane following calcium ionophore treatment and the subsequent production of leukotrienes. Rank order potency of MK886 anaologs correlated very nicely between inhibition of leukotriene synthesis and inhibition of 5-lipoxygenase translocation (Rouzer et al., *J. Biol. Chem.*, 265:1436–1442). These data suggest that antisense oligonucleotides directed against FLAP is an alternative strategy for inhibition of leukotriene production.

Phospholipases $A_2$ (EC 3.1.1.4) form a diverse family of enzymes which hydrolyze the sn-2 fatty acyl ester bond of membrane phospholipias producing free fatty acids such as arachidonic acid and lysophospholipids. Phospholipase $A_2$ ($PLA_2$) are found in a variety of snake and bee venoms and secreted in mammalian pancreatic fluid as a lipolytic enzyme. $PLA_2$ enzymes are also found in most mammalian tissues and are secreted into the extracellular medium from activated platelets and inflammatory cells. $PLA_2$ serves multiple roles in mammalian cells, including remodeling of cell membranes surfactant biosynthesis, digestive enzyme in pancreatic fluid, release from platelets and inflammatory cells as part of the inflammatory response, and release of arachidonic acid esterified to cellular phospholipids. Release of free arachidonic acid by $PLA_2$ is proposed to be the rate limiting step for prostaglandin biosynthesis and the critical first step in leukotriene and platelet activating factor biosynthesis. In addition to the liberation of precursors of inflammatory mediators, $PLA_2$ at high concentrations may be directly cytotoxic to cells by promoting cell lysis. The multiple functions which $PLA_2$ serves in the cell may explain the need for multiple $PLA_2$ enzymes. The $PLA_2$ isoenzyme found in inflammatory exudates (Pruzanski and Vadas, *J. Rheumatol.*, 15:1601–1603, 1988) is of particular interest as an antisense oligonucleotide target. This enzyme not only may play a role in the release of arachidonic acid from cellular membranes for eicosanoid biosynthesis, but may have a direct cytotoxic effect at the site of release.

Recently Seilhamer et al. (*J. Biol. Chem.*, 264:5335–5338, 1989) and Kramer et al. (*J. Biol. Chem.*, 264:5768–5775, 1989) reported the cDNA and genomic cloning, respectively of a human $PLA_2$ present in rheumatoid arthritis patients synovial fluid. The gene for the $PLA_2$ isolated from human synovial fluid ($SF-PLA_2$) was 4.5 kilobases in length and is processed to a mRNA 800 bases in length. The cDNA clone encodes a protein 144 amino acids in length, with the first 20 amino acids processed as a signal peptide for secretion from cells. The amino acid sequence of $SF-PLA_2$ is distinct from pancreatic $PLA_2$, more closely related to group II $PLA_2$ enzymes such as those present in rattlesnake venom.

$PLA_2$ is a low abundance protein in non-pancreatic tissues and fluids, comprising 0.01 to 0.001% of the total protein. The mRNA for $SF-PLA_2$ is also a low abundance mRNA which exhibits a limited tissue distribution. The limited tissue distribution, low abundance of the mRNA, correlation between enzyme activity and severity of the inflammatory disorder makes the $SF-PLA_2$ and attractive target for antisense oligonucleotide therapy.

Certain applications of antisense oligonucleotides and oligonucleotide analogs are apparent. For example, because gamma interferon increases $PLA_2$ synthesis in the presence of an interferon regulatory element in the 5'-nontranscribed region, antisense oligonucleotides may be used to inhibit the release of $PLA_2$ from gamma interferon treated human keratinocytes.

Antisense oligonucleotide therapy may also be useful in the treatment of inflammatory disorders of the skin, since $SF-PLA_2$ is secreted from a human epidermal carcinoma cell line and primary human epidermal keratinocytes. In addition, $PLA_2$ may play a mediating role in the inflammatory activity of gamma interferon in the skin since gamma interferon induced $PLA_2$ release from human keratinocytes.

Leukotriene $A_4$ hydrolase ($LTA_4$ hydrolase) catalyzes the hydrolysis of leukotriene $A_4$, formed by 5-lipoxygenase, to leukotriene $B_4$ a potent inflammatory mediator. $LTA_4$ hydrolase is a cytosolic protein-which has been purified to homogeneity from human lung (Ohishi et al., *J. Biol. Chem.*, 262:10200–10205, 1987), human leukocytes (Radmark et al., *J. Biol. Chem.*, 259:12339–12345, 1984) and human erythrocytes (McGee and Fitzpatrick, *J. Biol. Chem.*, 260:12832–12837). The enzymes purified from lung and leukocytes differed from the erythrocyte LTA$_4$ hydrolase in terms of molecular weight, kinetic properties and substrate preference. From the standpoint of human antisense oligonucleotide therapeutics, the leukocyte enzyme is of more interest than the erythrocyte LTA$_4$ hydrolase. Brythrocytes lack 5-lipoxygenase which is required for LTA$_4$ synthesis, therefore, these cells must rely upon LTA$_4$ released from activated neutrophils. The cDNA sequence for human LTA$_4$ hydrolase is known (Funk et al., *Proc. Natl. Acad. Sci USA*, 84:6677–6681, 1987; Minami et al., *J. Biol. Chem.*, 262:13873–13876, 1987). The 2250 nucleotide mRNA encodes for a 610 amino acid protein (FIG. 5) which contains no sequence similarities to other epoxide hydrolases. Therefore, inhibition of LTA$_4$ hydrolase with antisense oligonulceotides will have no effect on microsomal epoxide hydrolases.

Phospholipases C (EC 3.1.4.3) are a family of enzymes which hydrolyze the sn-3 phosphodiester bond in membrane phospholipids producing diacylglycerol and a phosphorylated polar head group. Mammalian phospholipase C (PLC) enzymes exhibit specificity for the polar head group which is hydrolyzed, i.e., phosphatidylcholine, phosphatidylinositol, etc. Recently, much interest has been generated in the those PLC enzymes which selectively hydrolyze phosphoinositide lipids in response to receptor occupancy by agonist. Hydrolysis of phosphatidylinositol 4,5-bisphosphate generates two second messenger molecules; diacylglycerol, a co-factor required for activation of protein kinase C, and inositol 1,4,5-trisphosphate, a soluble second messenger molecule which promotes the release of intracellular non-mitochrondrial stores of calcium (Berridge, *Ann. Rev. Biochem.*, 56:159–193, 1987). The diacylglycerol released may be further metabolized to free arachidonic acid by sequential actions of diglycerol lipase and monoglycerol lipase. Thus, phospholipases C are not only important enzymes in the generation of second messenger molecules, but may serve an important role in making arachidonic acid available for eicosanoid biosynthesis in select tissues.

Mammalian tissues contain multiple distinct forms of phosphoinositide-specific PLC (Crooke and Bennett, *Cell Calcium*, 10:309–323, 1989; Rhee et al., *Science*, 244:546–550, 1989). It is proposed that each of the enzymes couple to distinct classes of cell surface receptors, i.e., PLC-α couples to vasopressin receptors, PLC-δ couples to growth factor receptors, etc. (Aiyar et al., *Biochem. J.*, 261:63–70, 1989; Crooke and Bennett, *Cell Calcium*, 10:309–323 1989; Margolis et al., *Cell*, 57:1101–1107, 1989; Wahl et al., *Proc. Natl. Acad. Sci. USA*, 86:1568–1572, 1989). Because of the heterogeneity of PI-PLC enzymes it is possible to selectively inhibit the signal transduction pathway of proinflammatory agonists without effecting the signal transduction pathway of noninflammatory agonists.

To date, the cDNA for 6 distinct PI-PLC enzymes have been cloned. The enzymes range in size from 504 amino acids to 1250 amino acids, and are remarkably divergent considering that the exhibit similar biochemical properties. Four of the five enzymes (PLC-β, PLC-δ1, PLC-δ2, and PLC-α) contain two domains approximately 250 amino acids in length which exhibit between 50 to 80% sequence similarity. PLC-α contains sequences with 35% similarity to the first domain only (Crooke and Bennett, *Cell Calcium*, 10:309–323, 1989). The marked differences in DNA sequences for the different PI-PLC enzyme allows the selective targeting of one PI-PLC enzyme, without affecting other enzymes using antisense technology. The human cDNA clone has been reported only for PLC-δ2 (FIG. 6), (Ohta et al., *FEBS Lett.*, 242:31–35, 1988). The rest are rat cDNA clones. The genomic clones have not been reported for any of the PI-PLC enzymes.

All mammalian tissues which have been studied exhibit one or more PI-PLC enzymes. Generally, more than one enzyme exists in a single mammalian cell type. PI-PLC enzymes do exhibit tissue selectivity in their distribution. PLC-β is found predominantly in neural tissues and is the major enzyme in the brain. PLC-δ1 is found in brain and many peripheral tissues. PLC-δ2 is found in immune cells, and PLC-α appears to be predominantly in peripheral tissues. To date, a PI-PLC enzyme found exclusively in inflammatory cells has not been reported. However, PI-PLC-δ2 appears to be an important enzyme in immunocompetent cells (Emori et al., *J. Biol. Chem.*, 264:21885–21890). The protein is a moderately abundant protein comprising 0.1 to 0.05% of total cytosolic protein. No information is available concerning the genetic regulation of PI-PLC enzymes, mRNA or protein stability.

Coenzyme A-independent transacylase catalyzes the transfer of $C_{20}$ and $C_{22}$ polyunsaturated fatty acids from diacyl-phospholipids to lysophospholipids (FIG. 7). Arachidonic acid being a 20 carbon fatty acid with 4 double bonds at position 5, 8, 11, and 14. Coenzyme A-independent transacylase is an important enzyme in the generation of arachidonyl containing ether phospholipids which serve as a precursor for platelet activating factor and leukotrienes (FIG. 7). Coenzyme A-independent transacylase is an integral membrane protein localized to the microsomal membrane, with an apparent molecular weight of 50–60 kDa as determined by gel filtration chromatography (C. F. Bennett, unpublished data). The enzyme is unique in that it does not require coenzyme A for activity, unlike other fatty acid transacylases or acyltransferases. In addition, it exhibits rather strict specificity for both the donor lipid species and the acceptor lipid. The enzyme prefers diacyl phosphatidylcholine species containing $C_{20}$ or $C_{22}$ polyunsaturated fatty acids in the sn-2 position as the donor lipid (Sugiura et al., *J. Biol. Chem.*, 262:1199–1205, 1987). Phosphatidyl-ethanolamine was less effective as a donor lipid species than phosphatidylcholine, and phosphatidylinositol did not serve as a fatty acid donor. Fatty acids less than 20 carbons in length, such as palmitic and linoleic acids, were transferred much less efficiently. The enzyme also exhibited specificity towards acceptor lysophospholipids. Lysophospholipids containing inositol, serine and phosphate as the polar head group did not serve as acceptors for coenzyme A-independent transacylation. 1-O-Alkyl lysophosphatidylcholine was the preferred acceptor lipid species with 1-alkenyl lysophosphatidylcholine, 1-acyl lysophosphatidylcholine, 1-alkenyl lysophosphatidylethanolamine, 1-alkyl lysophosphatidylethanolamine, and 1-acyl lysophosphatidylethanolamine each exhibiting approximately 50% the activity as that of 1-alkyl lysophosphatidylcholine as acceptor lipids.

For therapeutics, an animal suspected of having a disease which can be modulated by decreasing 5-lipoxygenase, 5-lipoxygenase activating protein, SF-PLA$_2$, PI-PLC-δ2, leukotriene A$_4$ hydrolase, and coenzyme A-independent transacylase, is treated by administering oligonucleotide in accordance with this invention. Persons of ordinary skill can easily determine optimum dosages, dosing methodologies and repetition rates. Such treatment is generally continued until either a cure is effected or a diminution in the diseased state is achieved. Long term treatment is likely for some diseases.

The present invention employs oligonucleotides and oligonucleotide analogs for use in antisense inhibition of the function of RNA and DNA corresponding to proteins capable of modulating arachidonic acid metabolism. In the context of this invention, the term "oligonucleotide" refers to a polynucleotide formed from naturally occurring bases and cyclofuranasyl groups joined by native phosphodiester bonds. This term effectively refers to naturally-occurring species or synthetic species formed from naturally-occurring subunits or their close homologs.

"Oligonucleotide analog", as that term is used in connection with this invention, refers to moieties which function similarly to oligonucleotides but which have non-naturally-occurring portions which are not closely homologous. Thus, oligonucleotide analogs may have altered sugar moieties or inter-sugar linkages. Exemplary among these are the phosphorothioate and other sulfur containing species which are known for use in the art. In accordance with some preferred embodiments, at least some of the phosphodiester bonds of the oligonucleotide have been substituted with a structure which functions to enhance the ability of the compositions to penetrate into the region of cells where the RNA or DNA whose activity to be modulated is located. It is preferred that such substitutions comprise phosphorothioate bonds, methyl phosphorothioate bonds, or short chain alkyl or cycloalkyl structures. In accordance with other preferred embodiments, the phosphodiester bonds are substituted with other structures which are, at once, substantially non-ionic and non-chiral. Persons of ordinary skill in the art will be able to select other linkages for use in practice of the invention.

Oligonucleotide analogs may also include species which include at least some modified base forms. Thus, purines and pyrimidines other than those normally found in nature may be so employed. Similarly, modifications on the cyclofuranasyl portions of the nucleotide subunits may also occur, as long as the essential tenets of this invention are adhered to.

Such analogs are best described as being functionally interchangeable with natural oligonucleotides (or synthesized oligonucleotides along natural lines), but which have one or more differences from natural structure. All such analogs are comprehended by this invention, so long as they function effectively to hybridize with RNA and DNA deriving from a gene corresponding to one of the proteins capable of modulating arachidonic metabolism. The oligonucleotides and oligonucleotide analogs in accordance with this invention preferably comprise from about 3 to about 50 subunits. It is more preferred that such oligonucleotides and analogs comprise from about 8 to 25 subunits, and still more preferred to have from about 12 to 22 subunits. As will be appreciated, a subunit is a base-sugar combination suitably bound to adjacent subunits through phosphodiester or other bonds.

The oligonucleotides and analogs used in accordance with this invention may be conveniently and routinely made through the well-known technique of solid phase synthesis. Equipment for such synthesis is sold by several vendors, including Applied Biosystems. Any other means for such synthesis may also be employed, however, the actual synthesis of the oligonucleotides are well within the talents of the routineer.

It is also well known to use similar techniques to prepare other oligonucleotide analogs such as the phosphorothioates and alkylated derivatives.

In accordance with this invention, persons of ordinary skill in the art will understand that messenger RNA identified by the open reading frames (ORFs) of the DNA from which they are transcribed includes not only the information from the ORFs of the DNA, but also associated ribonucleotides which form a region known to such persons as the 5' untranslated region, the 3' untranslated region, and intron/exon junction ribonucleotides. Thus, oligonucleotides and oligonucleotide analogs may be formulated in accordance with this invention which are targeted wholly or in part to these associated ribonucleotides as well as to the informational ribonucleotide. In preferred embodiments, the oligonucleotide or analog is specifically hybridizable with a transcription initiation site, a translation initiation site, or an intron/exon junction. Most preferably, the oligonucleotide or oligonucleotide analog is specifically hybridizable with sequences adjacent to the 5' cap site.

In accordance with this invention, the oligonucleotide is specifically hybridizable with nucleic acids encoding a protein which modulates the synthesis or metabolism of arachidonic acid. In preferred embodiments, said proteins are 5-lipoxygenase, 5-lipoxygenase activating protein, phospholipase $A_2$, $LTA_4$ hydrolase, phospholipase C, and coenzyme A independent transacylase. Oligonucleotides or analogs comprising the corresponding sequence, or part thereof, are useful in the invention. For example, FIG. 3 is a human 5-lipoxygenase mRNA sequence; FIG. 4 is a human synovial fluid $PLA_2$ mRNA sequence; FIG. 5 is a human 5-lipoxygenase activating protein sequence; FIG. 6 is a human $LTA_4$ hydrolase mRNA sequence; and FIG. 7 is a human phosphoinositide-specific phospholipase C mRNA sequence. Oligonucleotides or analogs useful in the invention comprise one of these sequences, or part thereof. Thus, it is preferred to employ any of these oligonucleotides (or their analogs) as set forth above, or any of the similar nucleotides which persons of ordinary skill in the art can prepare from knowledge of the preferred antisense targets for the modulation of the synthesis or metabolism of arachidonic acid.

Several preferred embodiments of this invention are exemplified in accordance with the following examples. The target mRNA species for modulation relates to 5-lipoxygenase. Persons of ordinary skill in the art will appreciate that the present invention is not so limited, however, and that it is generally applicable. The inhibition or modulation of production of the enzyme 5-lipoxygenase is expected to have significant therapeutic benefits in the treatment of disease. In order to assess the effectiveness of the compositions, an assay or series of assays is required.

EXAMPLES

Example 1

Figure 8:
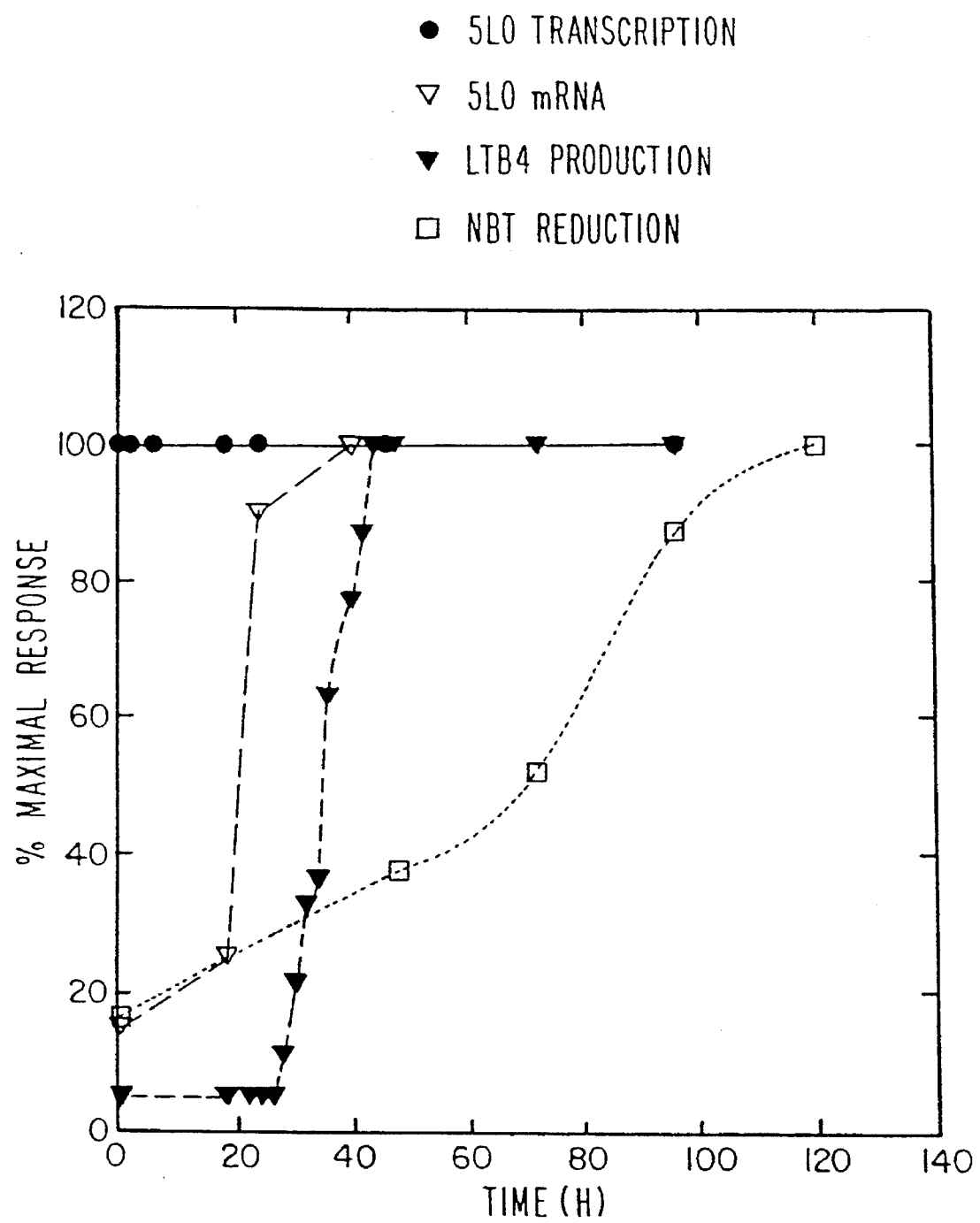
FIG. 8 is a graphical representation of the kinetics of 5-lipoxygenase induction in HL-60 cells.

The cellular assays for 5-lipoxygenase use the human promyelocytic leukemia cell line HL-60. These cells can be induced to differentiate into either a monocytic-like cell or neutrophil-like cell by various known agents. Treatment of the cells with 1.3% dimethyl sulfoxide (DMSO) is known to promote differentiation of the cells into neutrophils. It has now been found that basal HL-60 cells synthesize 5-lipoxygenase protein or secrete leukotrienes (a downstream product of 5-lipoxygenase) at the lower limit of current detection methods. Differentiation of the cells with DMSO causes an appearance of 5-lipoxygenase protein and leukotriene biosynthesis 48 hours after addition of DMSO. The induction kinetics of 5-lipoxygenase mRNA and leukotriene $B_4$ release from calcium ionophore stimulated HL-60 cells is shown in FIG. 8. Differentiation of the cells may also be accomplished with 1,25-dihydroxyvitamin $D_3$ and results in an eight to ten fold increase in 5-lipoxygenase enzyme activity at least 24 hours after addition of 1,25-dihydroxyvitamin $D_3$. Thus, induction of 5-lipoxygenase protein synthesis can be utilized as a test system for analysis of antisense oligonucleotides which interfere with 5-lipoxygenase synthesis in these cells.

An effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore $A_2 3187$. Leukotriene B4 released into the cell medium can be quantitated by radioimmunoassay, using commercially available diagnostic kits (New England Nuclear, Boston, Mass.). Leukotriene B4 production can he detected in HL-60 cells 48 hours following addition of DMSO to differentiate the cells into a neutrophil-like cell. Cells ($2 \times 10^5$ cells/mL) are treated with increasing concentrations of antisense oligonucleotides for 48–72 hours in the presence bf 1.3% DMSO. The cells are washed and resuspended at a concentration of $5 \times 10^6$ cell/mL in Dulbecco's phosphate buffered saline containing 1% delipidated bovine serum albumin. Cells are stimulated with 10 μM calcium ionophore $A_2 3187$ for 15 minutes, and the quantity of LTB4 produced from $5 \times 10^5$ cell determined by radioimmunoassay as described by the manufacturer.

Example 2

A second test system for antisense oligonucleotides makes use of the fact that 5-lipoxygenase is a "suicide" enzyme in that it inactivates itself upon reacting with substrate. Treatment of differentiated HL-60 or other cells expressing 5 lipoxygenase, with 10 μM $A_2 3187$, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from $A_2 3187$ treatment as measured by their ability to synthesize leukotriene $B_4$.

Figure 9:
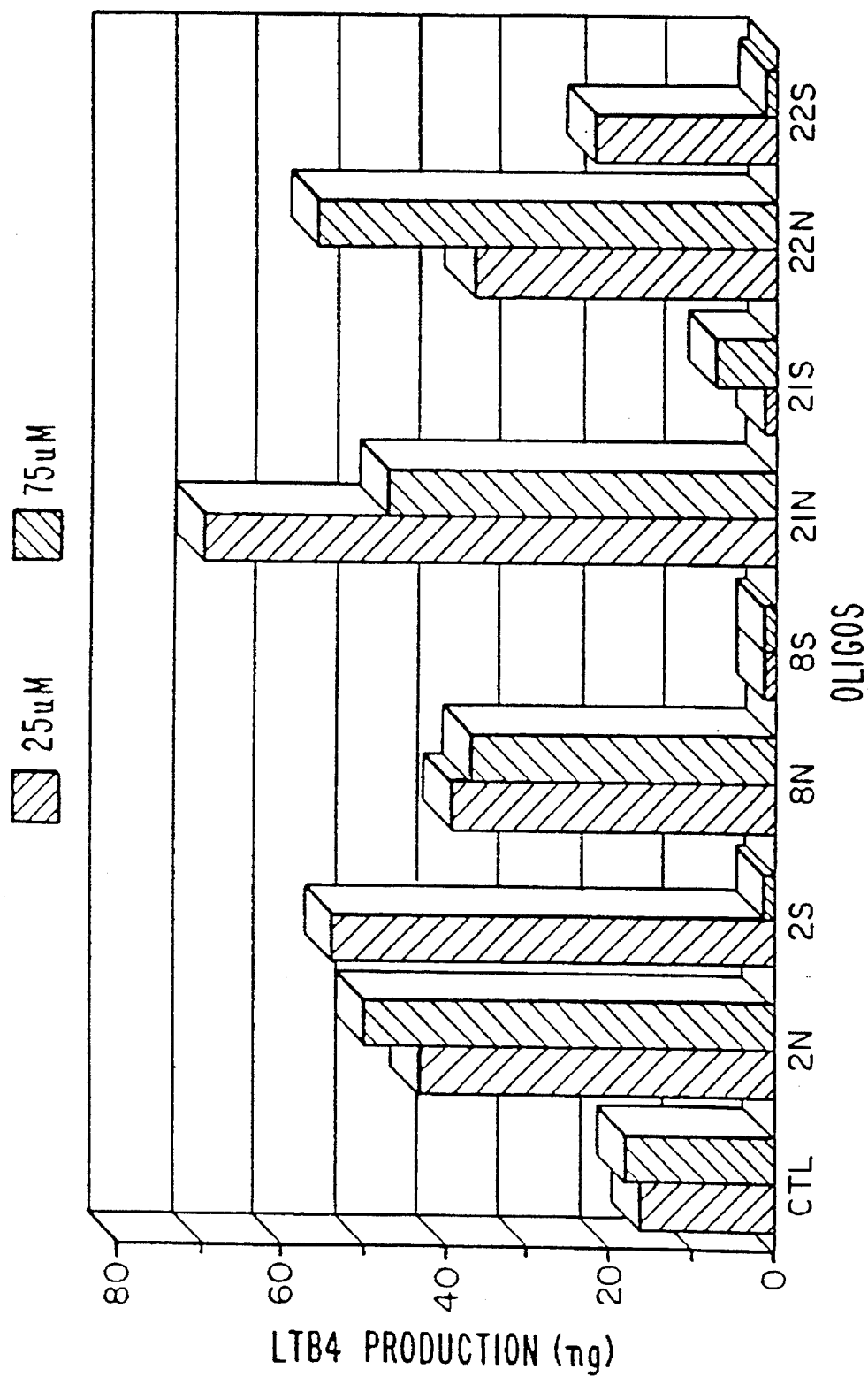
FIG. 9 is a graphical representation of the antisense oligonucleotide inhibition of 5-lipoxygenase expression in HL-60 cells.

Preliminary data demonstrate that antisense oligonucleotides have an effect in this model system (FIG. 9). HL-60 cells were differentiated with DMSO for 72 hours, treated with 10 μM $A_2 3187$ and washed three times in phosphate buffered saline to remove the ionophore. The cells were resuspended in RPMI-1640 containing 10% fetal bovine serum at a concentration of $1 \times 10^6$ cells/ml and the oligonucleotides added to a final concentration of either 25 μM or 75 μM. The oligonucleotides used are shown below with N indicating a phosphodiester linkage and S indicating a phosphorothioate linkage.

2N & 2S: 5'-ACGGTGACCGTGTAGGAGGGCATGGCGCGG-3'

8N & 8S: 5'-AATGGTGAATCTCACGTGTGCCACCAGCAG-3'

21N & 21S: 5'-AGGTGTCCGCATCTA-3'

22N & 22S: 5'-TCGGCGCGGCGGTCCAGGTGTCCGTATCTA-3'

The results suggest that phosphodiester oligonucleotides were not active in the assay, however, the analogous phosphorothioate oligonucleotide exhibited varying degrees of activity (FIG. 9). The most active oligonucleotide, 8S, targeted the 3' side of the intron/exon junction for intron H.

Example 3

The most direct effect which antisense oligonucleotides exert on intact cells which can be easily be quantitated is specific inhibition of 5-lipoxygenase protein synthesis. To perform this technique, cells are labelled with $^{35}$S-methionine (50 μCi/mL) for 2 hours at 37° C. to label newly-synthesized protein. Cells are extracted to solubilize total cellular proteins, and 5-lipoxygenase is immunoprecipitated with 5-lipoxygenase antibody. The immune complexes are trapped with protein A Sepharose beads. The inununoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipated from control cells would be normalized to 100%. Treatment of cells with 1 μM, 10 μM, and 30 μM of effective antisense oligonucleotide for 48 hours would reduce immunoprecipitated 5-LO to 5%, 25%, and 75% of control, respectively.

Example 4

Measurement of 5-lipoxygenase enzyme activity in cellular homogenates is also useful to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EGTA. The cell homogenate is centrifuged at 8,000× g for 15 minutes and the supernatants analyzed for 5-lipoxygenase activity. Cytosolic proteins are incubated with 10 μM $^{14}$C-arachidonic acid, 2 mM ATP, 50 μM free calcium, and 50 mM bis-Tris buffer, pH 7.0, for 10 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radio-chromatography detector. The amount of arachidonic acid converted into di-HETE's, 5-HPETE, and 5-HETE are used as a measure of 5-lipoxygenase activity.

Figure 10:
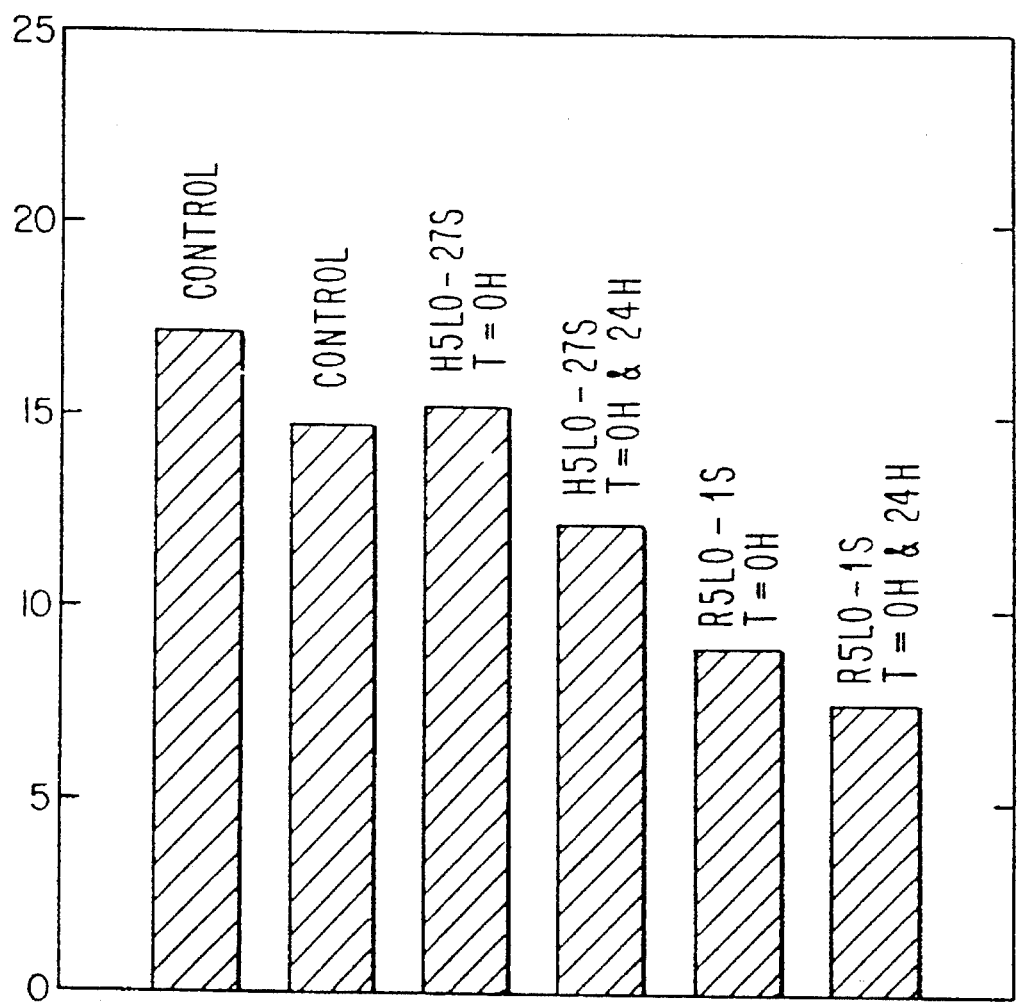
FIG. 10 s a graphical representation of antisense oligonucleotide inhibiton of 5-lipoxygenase expression in rat basophilic leukemia cells.

Preliminary data using quantitation of enzyme activity as a means of detecting effects of antisense oligonucleotides on 5-lipoxygenase expression is shown in FIG. 10. A rat basophilic leukemia cell line, RBL-1 cells, which expresses high amounts of 5-lipoxygenase activity under basal conditions were used for the assay. Cells were either treated for 48 hours with 50 μM oligonucleotide or for 24 hours with 50 μM oligonucleotide, then an additional 50 μM oligonucleotide was added and the cells incubated for an additional 24 hours. The cells were harvested and the amount of 5-lipoxygenase enzyme activity using 10 μg protein of 5000× g supernatant. The oligonucleotides used contained phosphorothioate linkages. The sequence of the oligonucleotides were:

r5LO-1S:5'-AGGCATGGCTCTGGGAAGTG-3'

H5LO-27S:5'-CGACTCCGTGCTGGCTCTGA-3'

The oligonucleotide r5LO-1S corresponds to sequences hybridizing to the AUG translation initiation codon of the rat 5-lipoxygenase mRNA, while H5LO-27S is a control oligonucleotide with a random sequence which does not hybridize to any known cellular RNA's. The results demonstrate that under both treatment condition the antisense oligonucleotide to 5-lipoxygenase reduced the enzyme activity 48% and 56%, respectively. The control oligonucleotide H27S did not significantly reduce 5-lipoxygenase activity when given as a single dose and inhibited activity by 17% when given as a double dose (FIG. 10).

Example 5

Antisense oligonucleotides were also tested for their ability to inhibit 5-lipoxygenase activity in 1,25-dihydroxyvitamin D$_3$ differentiated HL-60 cells. For oligonucleotide treatment, cells were washed three times in serum free medium (Opti-MEM) and resuspended at a concentration of 4×10$^6$ cells/mi. Five ml of cell suspension were placed in a 25 cm$^2$ tissue culture flask for each oligonucleotide treatment. To each flask, 32 μM commercial DOTMA was added to enhance oligonucleotide uptake and 1 μM of each antisense oligonucleotide. Cells were incubated for 4 hours in the presence of DOTMA and oligonucleotide at 27° C., then centrifuged at 400× g for 10 minutes to pellet the cells. Cell pellets were resuspended in 10 ml RPMI 1640 medium containing 10% fetal bovine serum, 10 μM oligonucleotide and 0.1 μM 1,25-dihydroxyvitamin D$_3$. Following differentiation for 84 hours, 5-lipoxygenase enzyme activity was determined as described in Example 4, using 100 μg of cellular homogenate.

The antisense oligonucleotides used in this series of experiments were phosphorothioate oligonucleotides having the sequences:

5'-....-3'
ISIS 1820 CGGTCCAGGTGTCCGCATCT - hybridizes to 5'-CAP sequences

ISIS 1821 CATGGCGCGGGCCGCGGG - hybridizes to AUG codon

ISIS 1821 GACCGTGTAGGAGGGCAT - hybridizes to AUG codon

Figure 11:
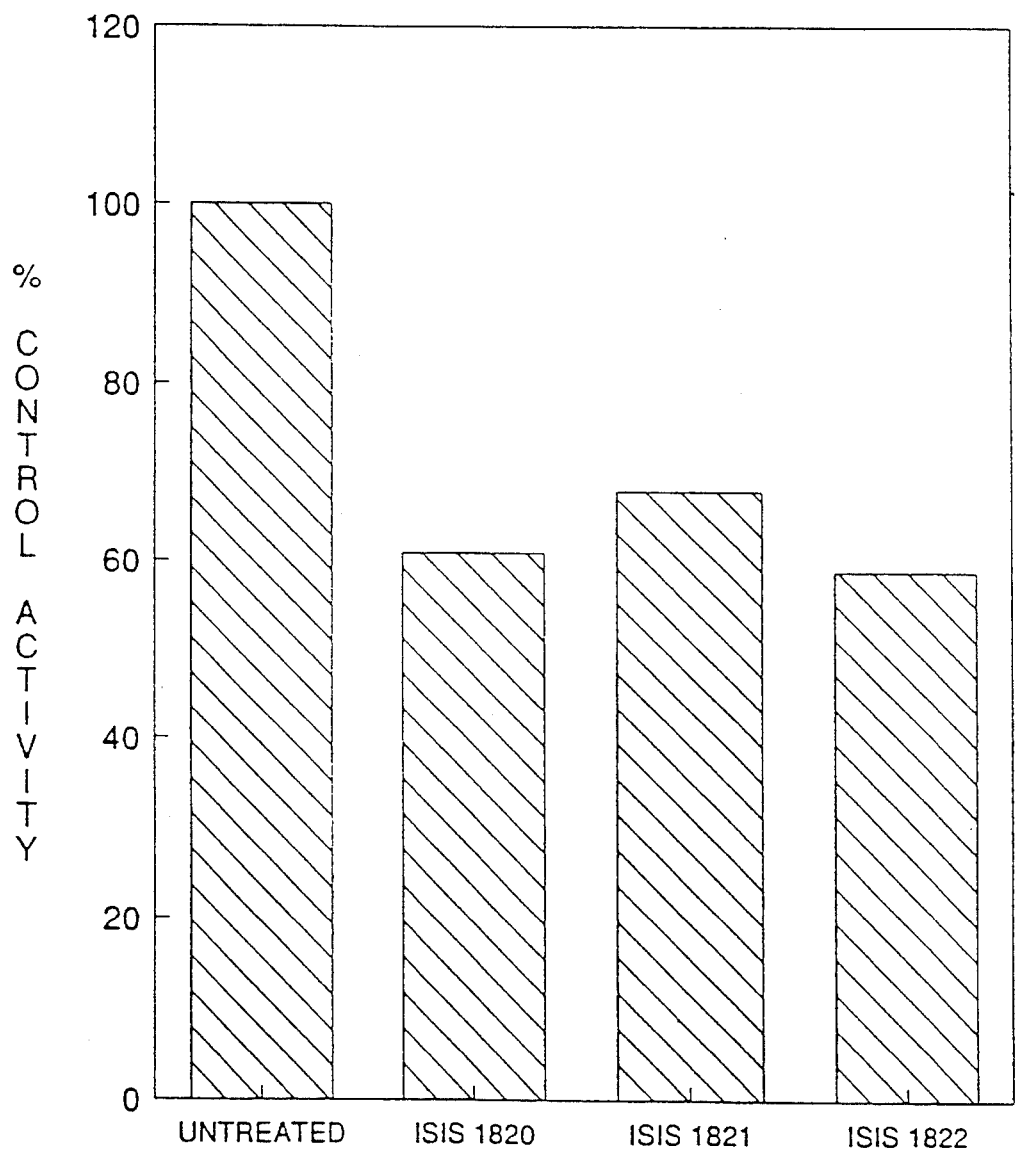
FIG. 11 is a graphical representation of antisense oligonucleotide inhibition of 5-lipoxygenase expression in vita D$_3$ differentiated HL-60 cells.

ISIS 1820, ISIS 1821 add ISIS 1822 decreased 5-lipoxygenase enzyme activity 60.9%, 67.9% and 58.8% respectively, compared to non-oligonucleotide treated cells (FIG. 11). These data demonstrate the utility of antisense oligonucleotides in inhibiting 5-lipoxygenase expression in a human cell line.

Example 6

Antisense oligonucleotides are also effective in inhibiting 5-lipoxygenase expression in rat cells. Rat basophilic leukemia cells (RBL-1) constitutively express twenty fold more 5-lipoxygenase enzyme activity than differentiated HL-60 cells. RBL-1 cells were treated with 1 μM oligonculeotide in the presence of 16 μM DOTMA for 4 hours in serum free medium. Thereafter, cells were incubated with 5 μM oligonucleotide in DMEM medium containing fetal calf serum. The half-life for 5-lipoxygenase is approximately 24 hours, therefore, the cells were treated with oligonucleotide for 5 days. At the end of 5 days, cells were sonicated and 5-lipoxygenase activity in cell extracts determined, as described in Example 4.

Figure 12:
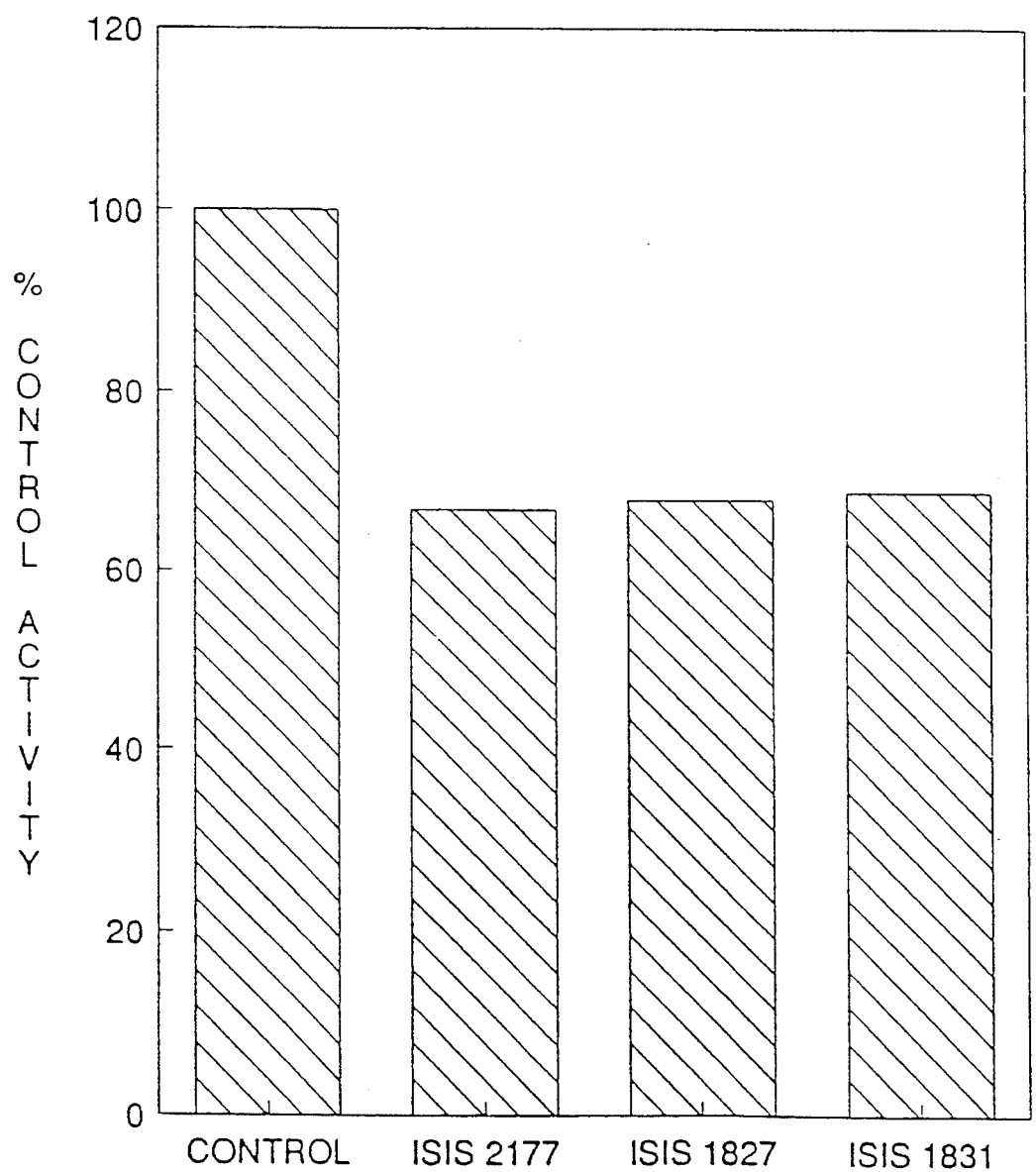
FIG. 12 is a graphical representation of antisense oligonucleotide inhibition of 5-lipoxygenase expression in RBL-1 rat cells.

Oligonucleotides ISIS 2177, ISIS 1827, and ISIS 1831 all reduced 5-lipoxygenase enzyme activity 35% (FIG. 12). The oligonucleotides all had phosphorothioate linkages and had the following sequences:

SEQ ID NO. 1

5'-....-3'
(ISIS 2177) AAGGCATGGCTCTGGGAAGTG -
Hybridizes to AUG codon

SEQ ID NO. 2
(ISIS 1827) ACATGGGCTA CCAGCAGCTGGGTGG -
hybridizes to intron/exon junction

SEQ ID NO. 3

-continued
(ISIS 1831) TTGACTCTGTCACTCAAGAG -
hybridizes to intron/exon junction

Example 7

Figure 13:
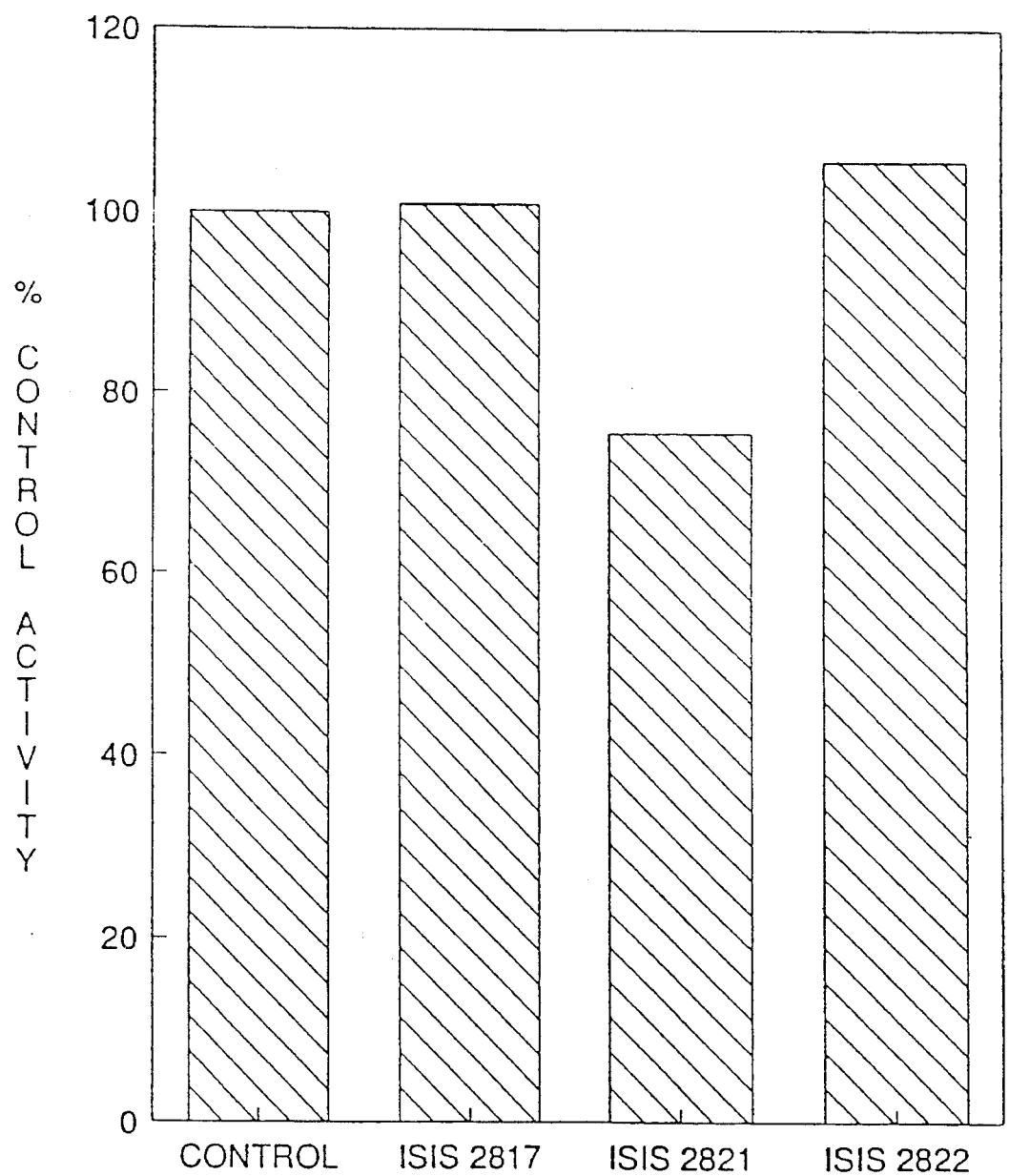
FIG. 13 is a graphical representation of antisense oligonucleotide inhibition of specific regions of 5-lipoxygenase mRNA in RBL-1 rat cells.

Another series of antisense oligonucleotide inhibition reactions provided evidence that specific regions of the mRNA are more sensitive to inhibition with antisense oligonucleotides. RBL-1 cells were treated with oligonucleotides, as described in Example 6, and cells were assayed for 5 lipoxygenase enzyme activity 5 days following treatment with oligonucleotides. Cells were treated with oligonucleotides ISIS 2817, ISIS 2821, and ISIS 2822, however, only ISIS 2821, which hybridizes to 3'-untranslated sequences, inhibited 5-lipoxygenase enzyme activity (FIG. 13). The oligonucleotides were all phosphorothioate oligonucleotides having the following sequences:

SEQ ID NO 4

5'-....-3'
(ISIS 2817) GGAAGGCATGGCTCTGGGAA - Hybridizes to AUG codon

SEQ ID NO. 5
(ISIS 2821) GCCTGCCCAGAGAGCTGCTG - Hybridizes to 3'-untranslated sequences SEQ ID NO. 6
(ISIS 2822) GGAAGATCTACAGCCTGCCA - Hybridizes to 3'-untranslated sequences.

Example 8

Inhibition of the production of 5-lipoxygenase in the mouse can be demonstrated in accordance with the following protocol. Topical application of arachidonic acid results in the rapid production of leukotriene B$_4$, leukotriene C$_4$ and prostaglandin E$_2$ in the skin, followed by edema and cellular infiltration. Certain inhibitors of 5-lipoxygenase have been shown to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene B$_4$ produced in biopsy specimens is performed as a direct measurement of 5-lipoxygenase activity in the tissue. Antisense oligonucleotides are applied topically to both ears 12 to 24 hours prior to administration of arachidonic acid to allow optimal activity of the compounds.

Example 9

Inhibition of the expression of 5-lipoxygenase for the treatment of allergic and inflammatory disorders and trauma.

Representative molecules that fall within the scope of this invention are described below. The first three molecules described in this example preferably bind to 5-lipoxygenase mRNA. A fourth molecule binds to the 5-lipoxygenase gene forming a triple stranded structure, thus modulating the amount of mRNA made from the 5-lipoxygenase gene.

1) In the first representative molecule, the base sequence is complementary to the 5-lipoxygenase mRNA beginning at the initiation codon and extending into the reading frame, hybridizing to a total of 15 ribonucleotide units of the 5-lipoxygenase mRNA:

MetProSer ...
5'- ... CGCCATGCCCTCCTACACGGTCACCGTGGCCACT ... 3'
3'-TACGGGAGGATGTGC-5'

2) The second representative molecule is complementary to the 12 contiguous ribonucleotides that precede the translational termination signal of the 5-lipoxygenase mRNA.

SerValAlaIle
5'- ... CCGAACAGTGTGGCCATCTGAGCACAC ... 3'
3'-TCACACCGGTAG-5'

3) The third representative molecule is complementary to 30 contiguous ribonucleotides near the 5' end of the 5'lipoxygenase mRNA, and also includes the sequence described in the first representative molecule directed to 5-lipoxygenase.

5'- ... CCCCGGCCCGCGCCATGCCCTCCTACACGGT ... -3'
3'-GGGGCCGGGCGCGGTACGGGAGGATGTGCCA ... -5'

4) The fourth representative molecule will bind to the DNA of the 5-lipoxygenase gene forming a triple stranded structure that would modulate expression of the gene.

5'-GGGCGGGGGCGGGGGCGGGGGCGGGGGCGGGGGCAGCCGGGAGCCTGGA-3'
3'-CCCGCCCCCGCCCCGCCCCGCCCCCGCCCCCGTCGGCCCTCGGACCT-5'
PYYYYYPYYYYYPYYYYYPYYYYYPYYPP

Where a number of specific embodiments have been set forth, the present invention is to be limited only in accordance with the following claims.

Example 10

There are several $PLA_2$ isoenzymes expressed in mammalian cells. Before antisense oligonucleotides can be tested for inhibition of synovial fluid $PLA_2$, it was necessary to identify human cell lines which express the appropriate isoenzymes. Over twenty human cell lines were screened for the presence of SF-$PLA_2$ by Northern blot analysis and polymerass chain reaction. Two Cell lines were identified as expressing the SF-$PLA_2$, A431 cells and primary human keratinocytes. As predicted from the cDNA sequence of SF-$PLA_2$, (FIG. 4), both cell lines secrete $PLA_2$ enzyme into the medium. The $PLA_2$ enzyme activity may be measured by either the *E. coli* assay or 1-palmitoyl, 2-$^{14}$C-arachidonyl phosphatidylethanolamine, as described in Example 11. The pH optima, calcium requirements, and substrate specificity for the secreted enzymes were the same as previously reported for the SF-$PLA_2$ (Kramer, et al., *J. Biol. Chem.*, 264:5768–5775).

Figure 14:
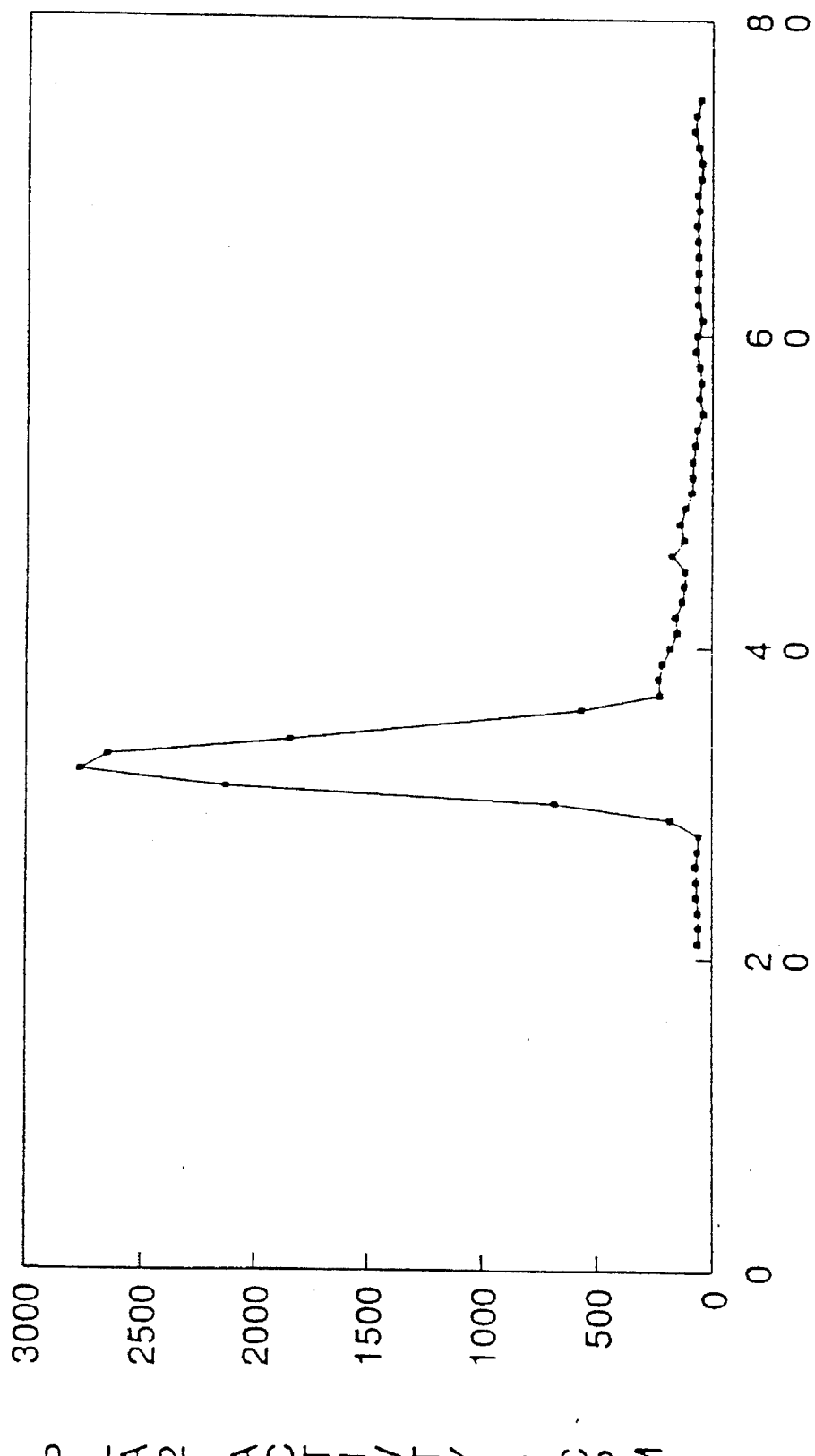
FIG. 14 is a graphical representation of HPLC analysis of secreted PLA$_2$ from A431 cells.

Reverse phase HPLC analysis of the tissue culture supernatant indicated that only one $PLA_2$ isoenzyme is secreted from A431 cells. Cell culture supernatant was clarified by centrifugation at 14,000× g for 10 minutes. The clarified supernatant (2 ml) was applied to a $C_4$ silica matrex column equilibrated with 0.1% TFA. Protein was eluted from the column with a linear 60 ml 0% to 100% acetonitrile gradient at 1 ml/min. Fractions were collected (1 ml) and assayed for $PLA_2$ enzyme activity, as described in Example 11. The results demonstrate that only one $PLA_2$ enzyme is secreted from A431 cells (FIG. 14). Therefore, an assay which could be used to test antisense oligonucleotide inhibition of SF-$PLA_2$ synthesis would be to treat A431 cells grown to confluence in 24 well plates with 1 µM oligonucleotide plus 40 µM DOTMA in serum free medium for six hours. The medium is replaced with DMEM medium containing 1 mg/ml bovine serum albumin and 10 µM oligonucleotide. The amount of $PLA_2$ secreted into tissue culture medium 24 hours after addition of DMEM containing 1 mg/ml BSA would be determined as described in Example 11.

Figure 15:
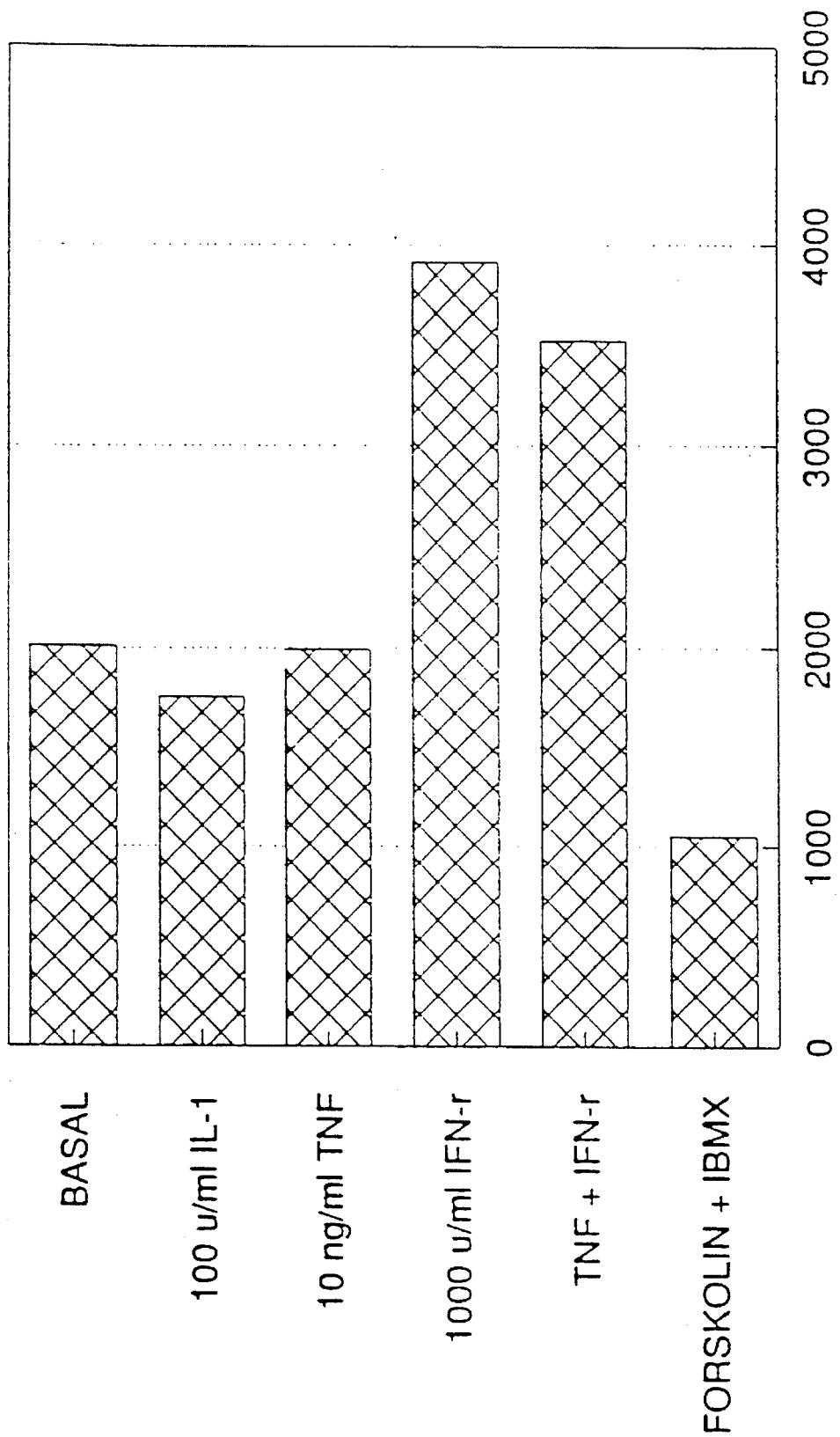
FIG. 15 is a graphical representation of increased secretion of PLA$_2$ caused by primary human keratinocytes.

We have demonstrated that interferon-γ, but not interleukin 1β, tumor necrosis factor-α, or forskolin plus isobutyl methylxanthanine, increased the secretion of SF-$PLA_2$ into the medium, measured in counts per minute, cpm (FIG 15). Supporting our finding that interferon-γ increases $PLA_2$ synthesis is the presence of an interferon regulatory element in the 5'- nontranscribed region of the SF-$PLA_2$ gene. Antisense oligonucleotides could, therefore, be used to inhibit the release of $PLA_2$ from interferon-γ treated human keratinocytes. The cells, grown in 24-well plates, would be treated with 1 µM antisense oligonucleotide plus 32 µM DOTMA in serum-free medium for 4 hours. Following the 4 hr treatment in serum free medium, the medium would be replaced with KGM (Clonetics, San Diego, Calif.) and 5 µM oligonucleotide and incubated for an additional 3 hours. Interferon-γ would be added to the cells (300 units/ml) and the amount of $PLA_2$ enzyme activity secreted from the cells would be determined 24 hr following the addition of interferon-γ.

The fact that we have been able to detect SF-$PLA_2$ secretion from a human epidermal carcinoma cell line (A431 cells) and primary human epidermal keratinocytes suggests that antisense oligonucleotides which inhibit SF-$PLA_2$ expression would be useful in the treatment of inflammatory disorders of the skin. In addition, we have found that interferon-γ induces $PLA_2$ release from human keratinocytes, possibly mediating in part the inflammatory activity of interferon-γ in the skin.

The following oligonucleotides or oligonucleotide analogs would be useful in inhibiting SF-$PLA_2$ expression.

5'- .... -3'
TTCATGGTAAGAGTTCTTGGG (SEQ ID NO. 7)
TCTGCCCCGGCCGTCGCTCCC (SEQ ID NO. 8)
CAAAGATCATGATCACTGCCA (SEQ ID NO. 9)
TCCCATGGGCCTGCAGTAGGC (SEQ ID NO. 10)
CCTGCAGTAGGCCTGGAAGGA (SEQ ID NO. 11)
GGAAGGTTTCCAGGGAAGAGG (SEQ ID NO. 12)
CAGAGGACTCCAGAGTTGTAT (SEQ ID NO. 13)
GGGTGGGTATAGAAGGGCTCC (SEQ ID NO. 14)

Example 11

In vitro biochemical assays for $PLA_2$ enzyme activity are relatively easy assays to perform and can be configured to a high throughput assay. The most common assays measure the release of radiolabeled fatty acid from either *E. coli* prelabelled with $^{14}$C-fatty acid (Franson et al., *J. Lipid Res.*, 19:18–23, 1978) or pure phospholipid substrates (Bennett et al., *Biochem. Pharm.*, 36:733–740, 1987). Cellular assays for $PLA_2$ measure the release of fatty acids from cells prelabelled with radiolabelled arachidonic acid. Alternatively, in those cell systems which secrete $PLA_2$ into the extracellular medium, $PLA_2$ may be detected by a direct enzyme assay of the culture medium, as described above. We have identified expression of human synovial fluid $PLA_2$ (human SF-$PLA_2$) in the human epidermal carcinoma cell line A431.

A predicted result from an experiment treating A431 cells with an antisense oligonucleotide is described below. A431 cells are plated in 100 mm petri dishes and allowed to obtain confluence. The cells are treated with 1, 10, and 50 μM antisense oligonucleotide containing the sequence 5'GGTCTTCATGGTAAGAGTTCTTGG-3' for 36 hours at 37° C. Phospholipase $A_2$ enzyme activity was measured in crude cellular homogenates by the release of arachidonic acid from 1-acyl-2-[1-$^{14}$C]arachidonyl phosphatidylethanolamine (25 μM final concentration in 1 mg/ml deoxycholate). Antisense oligonucleotide reduced phospholipase $A_2$ enzyme activity to 3%, 60%, and 95% of control, following treatment with 1 μM, 10 μM, and 50 μM, respectively.

Example 12

In vivo assays for $PLA_2$ have not been well defined. One assay which is gaining popularity as a screen for $PLA_2$ inhibitors is the direct injection of purified $PLA_2$ into a rat paw. The resulting edema is quantitated as a measure of $PLA_2$ activity. This assay would be inappropriate as an antisense assay. Alternative assays which may prove useful for identify antisense oligonucleotides which inhibit the synthesis of $PLA_2$ include glycogen-induced ascites in rabbits, casein-induced peritonitis in rats, and gram negative septic shock in rabbits. In each of the model systems, an elevation of $PLA_2$ in the extracellular fluid has been documented.

Example 13

5-Lipoxygenase activating protein may be directly assayed by quantitating the amount of immunoreactive protein using an ELISA assay. Antibodies prepared against FLAP expressed in E. coli are used for the assay. E. coli expressed FLAP is also used as the standard to quantitate the assay. For the assay, HL-60 cells are treated with antisense oligonucleotides for 24 to 72 hours. The cells are disrupted by sonication and centrifuged at 5000× g for 15 minutes. The supernatant fraction are centrifuged at 100,000× g for 1 hour and the 100,000× g pellet extracted with 1% CHAPS detergent in 50 mM Tris-HCl, 140 mM NaCl, 0.5 mM DTT; pH=7.4. The solubilized membrane protein are used in a competitive ELISA assay. Recombinant FLAP (25 ng) is bound to each well of a microtiter plate overnight at 4° C. The wells of the plate are then blocked for 90 minutes with 5% goat serum in 20 mM Tris-HCl; pH=7.4, 150 mM NaCl (TBS). The cell extracts or purified FLAP standard are incubated with a 1:2000 dilution of FLAP polyclonal antibody in a total volume of 100 μL for 90 minutes. The wells are washed with TBS containing 0.05% tween 20 (TBST) and incubated with a 1:1000 dilution of biotinylated conjugated goat anti-rabbit IgG for 1 hour. The plates are washed with TBST again and incubated with a 1:1000 dilution of peroxidase conjugated streptavidin for 1 hour. The plates are washed again with TBST and the amount of peroxidase labelled streptavidin bound to the plates quantitated by development with tetramethylbenzidine.

Example 14

Inhibition of 5-lipoxygenase activating protein (FLAP) activity with antisense oligonucleotides may also be detected by inhibition of calcium ionophore induced translocation of 5-lipoxygenase from the cytosol to the membrane fraction of cells, and a subsequent inhibition of leukotriene formation. For the assay, differentiation of HL-60 cells model are used, as described under Example 1. Antisense oligonucleotides which hybridize to FLAP mRNA are added to the culture of HL60 cells at the time DMSO is added to differentiate the cells. The cells are assayed for FLAP activity 48 to 72 hours following the addition of DMSO to the culture medium. The cells are stimulated with 10 μM calcium ionophore for 15 minutes at 37° C. The cells are collected by centrifugation at 1000× g for 10 minutes. The amount of leukotriene $B_4$ synthesized by the cells and released into the supernatant is determined by radioimmunoassay, as described in Example 1. The cell pellet is washed one time with phosphate buffered saline and the cells disrupted by sonication, as described in Example 4. The 5000× g supernatant is centrifuged at 100,000× g for 1 hour and the amount of 5-lipoxygenase associated with the membrane fraction (100,000× g pellet) determined by Western blotting. Cytosolic and membrane proteins (100 μg each) are resolved on a SDS-polyacrylamide gel, transferred to nitrocellulose paper and incubated with 5-lipoxygenase antibody, followed by $^{125}$I-protein A (Bennett and Crooke, J Biol Chem., 262:18789–13797 1987). The nitrocellulose paper is then exposed for autoradiography and the amount of 5-lipoxygenase in each cellular fraction determined by scanning the autoradiographs by laser densitometry.

Example 15

Leukotriene $A_4$ hydrolase is determined by a direct enzyme assay of cytosolic fraction of cells treated with antisense oligonucleotides, as described by Ohishi et al. (J. Biol. Chem., 262:10200–10205, 1987). Briefly, HL-60 cells treated with antisense oligonucleotides are disrupted by sonication and cytosolic fraction isolated by centrifugation at 100,000× g for 1 hour. The reaction mixture contains 100 mM Tris-HCl buffer (pH=7.8) and enzyme in a total volume of 50 μL. After preincubating the enzyme for 3–4 minutes at 37° C., leukotriene $A_4$ in ethanol containing lithium hydroxide was added to a final concentration of 75 μM and a final ethanol concentration of 2%. The enzyme was incubated for 1 minute at 37° C. and the reaction terminated by the addition of 100 μL of acetonitrile/methanol/acetic acid, 150:50:3 (v/v/v) containing 0.3 nmol prostaglandin $B_2$ as an internal standard. Protein is precipitated by incubation at −20° C. for 30 minutes followed by centrifugation at 10,000× g for 10 minutes. A 120 μL aliquot of the supernatant was removed and 20 μL of 0.35% disodium EDTA is added. The amount of leukotriene B4 formed in 50 μL aliquot of the resulting solution is determined by reverse phase HPLC using a $C_{18}$ column. Samples are eluted isocratically with solvent containing acetonitrile/methanol/water/acetic acid (3:1:3:0.006, v/v/v/v, 0.05% disodium EDTA). The absorbance at 270 nm is monitored to quantitate the amount of leukotriene $B_4$ formed.

A predicted result from treatment of HL60 cells with a phosphorothioate antisense oligonucleotide having the following sequence 5'-TATCTCGGGCATGGCTCTGGG-3' hybridizing to sequences corresponding to the initiation of translation for leukotriene $A_4$ hydrolase is described. Cells were treated with 10 μM, 30 μM, and 75 μM oligonucleotide for 36 hours. The cells were harvested and the amount of $LTA_4$ hydrolase quantitated, as previously described. Treatment with antisense oligonucleotide reduced $LTA_4$ hydrolase enzyme activity by 0%, 15%, and 45%, respectively.

Example 16

Assays for PI-PLC enzyme activity in cell extracts utilize radiolabeled phosphoinositides as substrates which are commercially available (Hoffman and Majerus, J. Biol. Chem., 257:6461–6469, 1982). Enzyme assays for PI-PLC can be easily configured to high throughput assays. However, enzymatic assays do not discriminate for effects of compounds on specific PI-PLC isoenzymes, but instead, measure total PI-PLC activity in cellular extracts. To determine the effects of antisense oligonucleotides on a specific PI-PLC isoenzyme, it will be necessary to utilize an immunochemical assay. Antibodies specific for PI-PLC-δ2 are prepared by immunizing rabbits with a peptide such as NH$_2$-SKRKST-PERRTVQVT-COOH or similar peptides specific for PI-PLC-δ2 conjugated to keyhole limpet hemocyanin. The antibodies are used in a competitive ELISA assay, as described in Example 9.

Example 17

PI-PLC enzyme activity in intact cells can be directly measured by quantitating the formation of 3H-inositol phosphates, following agonist stimulation in cells prelabelled with 3H-inositol. For screening for effects of antisense oligonucleotides on PI-PLC-δ2 expression, HL-60 cells will be used. The cells are labeled with 20 µCi/ml $^3$H-myoinositol for 36 hours at 37° C. The antisense oligonucleotide which specifically hybridizes to PI-PLC-δ2 mRNA such as 5'-GTGGTGGACATTGTGGCCGCT-3' is added to the cells during the 36 hour labelling with $^3$H-myoinositol. The cells are washed with Hank's balanced salt solution (HBSS) to remove unincorporated $^3$H-myoinositol and resuspended at a final concentration of 5×10$^6$ cells/mi. Cells (0.3 ml) are then stimulated with the appropriate agonist (fMet-Leu-Phe, epidermal growth factor, GM-CSF, gamma-interferon, platelet derived growth factor, leukotriene D$_4$, etc.) for 2 min. at 37° C. Water soluble inositol phosphates are extracted with 0.93 ml chloroform/methanol (1:2, v/v), followed by 0.3 ml chloroform and 0.3 ml water. Inositol phosphates are separated by chromatography on Dowex AG1XS, as previously described (Betridge et al., *Biochem. J.*, 212:473–482, 1983).

Active compounds in the cell based assays can then be tested for activity in a variety of standard pharmacological assays, such carrageenan induced peritonitis, arachidonic acid induced inflammation in mice ears, etc.

Example 18

Coenzyme A-independent transacylase enzyme activity may be measured in microsomal fraction from cells treated with antisense oligonucleotides using $^3$H-1-alkyl lysophosphatidylcholine as a substrate. We have identified that the human promonocytic leukemia cell line, U937, is a good source for measuring coenzyme A-independent transacylase activity. Following treatment, for various periods of time cells are washed in phosphate buffered saline then suspended in 10 mM bis Tris; pH=7.0, 10 mM NaCl, 2 mM EGTA, 1 mM MgCl$_2$, 0.1 mM leupeptin, and 10 µg/ml aprotinin at a concentration of 10$^7$ cells/ml. The cells are disrupted by sonication 30% power and microsomal fraction obtained by differential centrifugation. The crude homogenate is centrifuged at 10,000× g for 20 min, the supernatant is then centrifuged at 100,000× g for 60 min. The 100,000× g pellet is resuspended in 10 mM phosphate, 150 mM NaCl; pH=7.4 and used for the assays. Between 10 and 50 µg of protein were incubated with 1 µM $^3$H-1-O-alkyl lysophosphatidylcholine, 1 mg/ml bovine serum albumin in a total volume of 100 µL for 10 minutes at 37° C. The reactions were terminated by the sequential addition of 100 µL chloroform:methanol (1:2), 100 µL chloroform, and 100 µL of 1 M KCl. The samples are vortexed and centrifuged at 10,000× g for 4 minutes. The material in the organic phase is spotted onto silica gel G plates and chromatographed using a solvent containing chloroform:methanol:acetic acid:water (100:60:16:8). The plates are stained with iodine vapor, the band corresponding to 1-alkyl, 2-arachidonyl phosphatidylcholine collected, and the amount of radioactive material determined in a liquid scintillation counter.

An expected result from treating U937 cells with an antisense phophorothioate oligonucleotide directed against coenzyme A-independent transacylase is described below. U937 cells are treated with 1, 10, and 50 µM antisense oligonucleotide 20 bases in length containing the sequence CAT at position 10–12, corresponding to the initiation of translation for 72 hours at 37° C. The cells are harvested and analyzed for coenzyme A-independent transacylase activity, as described above. Treatment with the drug at concentrations of 1, 10, and 50 µM reduced coenzyme A-independent transacylase activity by 4%, 22% and 72%, respectively.

What is claimed is:

1. A phosphorothioate oligonucleotide having a sequence: 5' . . . 3'
TCGGCGCGGCGGTCCAGGTGTCCGCATCTA,
ACGGTGACCGTGTAGGAGGGCATGGCGCGG,
AATGGTGAATCTCACGTGTGCCACCAGCAG,
AGGTGTCCGCATCTA,
CGGTCCAGGTGTCCGCATCT,
CATGGCGCGGGCCGCGGG,
GACCGTGTAGGAGGGCAT,
AGGCATGGCTCTGGGAAGTG,
AAGGCATGGCTCTGGGAAAGTG (SEQ ID NO. 1),
ACATGGGCTACCAGCAGCTGGGTGG (SEQ ID NO. 2),
TTGACTCTGTCACTCAAGAG (SEQ ID NO. 3), or
GCCTGCCCAGAGAGCTGCTG (SEQ ID NO. 5).

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:1:

AAGGCATGGC TCTGGGAAGT G                                                              2 1

( 2 ) INFORMATION FOR SEQ ID NO:2:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:2:

ACATGGGCTA CCAGCAGCTG GGTGG                            25

( 2 ) INFORMATION FOR SEQ ID NO:3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:3:

TTGACTCTGT CACTCAAGAG                                20

( 2 ) INFORMATION FOR SEQ ID NO:4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:4:

GGAAGGCATG GCTCTGGGAA                                20

( 2 ) INFORMATION FOR SEQ ID NO:5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:5:

GCCTGCCCAG AGAGCTGCTG                                20

( 2 ) INFORMATION FOR SEQ ID NO:6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:6:

GGAAGATCTA CAGCCTGCCA                                20

( 2 ) INFORMATION FOR SEQ ID NO:7:

( i ) SEQUENCE CHARACTERISTICS:
        ( A ) LENGTH: 21
        ( B ) TYPE: nucleic acid (C) STRANDEDNESS: single
(D) TOPOLOGY: linear (i v) ANTI-SENSE: yes (x i) SEQUENCE DESCRIPTION: SEQ ID NO:7:

TTCATGGTAA GAGTTCTTGG G    21

(2) INFORMATION FOR SEQ ID NO:8:

(i) SEQUENCE CHARACTERISTICS:
(A) LENGTH: 21
(B) TYPE: nucleic acid
(C) STRANDEDNESS: single
(D) TOPOLOGY: linear (i v) ANTI-SENSE: yes (x i) SEQUENCE DESCRIPTION: SEQ ID NO:8:

TCTGCCCCGG CCGTCGCTCC C    21

(2) INFORMATION FOR SEQ ID NO:9:

(i) SEQUENCE CHARACTERISTICS:
(A) LENGTH: 21
(B) TYPE: nucleic acid
(C) STRANDEDNESS: single
(D) TOPOLOGY: linear (i v) ANTI-SENSE: yes (x i) SEQUENCE DESCRIPTION: SEQ ID NO:9:

CAAAGATCAT GATCACTGCC A    21

(2) INFORMATION FOR SEQ ID NO:10:

(i) SEQUENCE CHARACTERISTICS:
(A) LENGTH: 21
(B) TYPE: nucleic acid
(C) STRANDEDNESS: single
(D) TOPOLOGY: linear (i v) ANTI-SENSE: yes (x i) SEQUENCE DESCRIPTION: SEQ ID NO:10:

TCCCATGGGC CTGCAGTAGG C    21

(2) INFORMATION FOR SEQ ID NO:11:

(i) SEQUENCE CHARACTERISTICS:
(A) LENGTH: 21
(B) TYPE: nucleic acid
(C) STRANDEDNESS: single
(D) TOPOLOGY: linear (i v) ANTI-SENSE: yes (x i) SEQUENCE DESCRIPTION: SEQ ID NO:11:

CCTGCAGTAG GCCTGGAAGG A    21

(2) INFORMATION FOR SEQ ID NO:12:

(i) SEQUENCE CHARACTERISTICS:
(A) LENGTH: 21
(B) TYPE: nucleic acid
(C) STRANDEDNESS: single
(D) TOPOLOGY: linear (i v) ANTI-SENSE: yes ( x i ) SEQUENCE DESCRIPTION: SEQ ID NO:12:

GGAAGGTTTC CAGGGAAGAG G    21

( 2 ) INFORMATION FOR SEQ ID NO:13:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:13:

CAGAGGACTC CAGAGTTGTA T    21

( 2 ) INFORMATION FOR SEQ ID NO:14:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:14:

GGGTGGGTAT AGAAGGGCTC C    21